(12) United States Patent
Jackson

(10) Patent No.: US 8,840,652 B2
(45) Date of Patent: *Sep. 23, 2014

(54) BONE ANCHORS WITH LONGITUDINAL CONNECTING MEMBER ENGAGING INSERTS AND CLOSURES FOR FIXATION AND OPTIONAL ANGULATION

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 88 days.

This patent is subject to a terminal disclaimer.

(21) Appl. No.: 13/694,032

(22) Filed: Oct. 22, 2012

(65) Prior Publication Data
US 2013/0060292 A1 Mar. 7, 2013

Related U.S. Application Data

(63) Continuation of application No. 12/804,999, filed on Aug. 3, 2010, now Pat. No. 8,308,782, which is a continuation-in-part of application No. 12/080,202, filed on Apr. 1, 2008, now Pat. No. 7,875,065, which is a continuation-in-part of application No. 11/281,818, filed on Nov. 17, 2005, now Pat. No. 7,625,396, said application No. 12/804,999 is a continuation-in-part of application No. 12/229,207, filed on Aug. 20, 2008, now Pat. No. 8,353,932, which is a continuation-in-part of application No. 11/522,503, filed on Sep. 14, 2006, now Pat. No. 7,766,915, which is a continuation-in-part of application No. 11/024,543, filed on Dec. 20, 2004, now Pat. No. 7,204,838.

(60) Provisional application No. 61/273,399, filed on Aug. 4, 2009, provisional application No. 60/630,478, filed on Nov. 23, 2004, provisional application No. 60/994,083, filed on Sep. 17, 2007.

(51) Int. Cl.
*A61B 17/86* (2006.01)

(52) U.S. Cl.
USPC .......................................................... 606/305

(58) Field of Classification Search
CPC ........... A61B 17/7008; A61B 17/7037; A61B 17/7032; A61B 17/7031; A61B 17/7082; A61B 17/7091
USPC .................................. 606/264–270, 300–309
See application file for complete search history.

(56) References Cited

U.S. PATENT DOCUMENTS

| 2,346,346 | A | 4/1944 | Anderson |
| 2,362,999 | A | 11/1944 | Elmer |

(Continued)

FOREIGN PATENT DOCUMENTS

| DE | 19507141 | 9/1996 |
| EP | 1121902 | 8/2001 |

(Continued)

OTHER PUBLICATIONS

*EBI Omega 21* Brochure, EBI Spine Systems, pub. 1999.

(Continued)

*Primary Examiner* — Pedro Philogene
(74) *Attorney, Agent, or Firm* — John C. McMahon

(57) ABSTRACT

Polyaxial bone anchors include a retainer for holding a shank within a receiver, the retainer being in at least two discrete pieces and cooperating with a variety of inserts, some of which independently lock the polyaxial mechanism. Polyaxial and mono-axial bone anchor assemblies include pivot and/or pressure inserts or pads that cooperate with longitudinal connecting members to provide a desired degree of continued control of angulation of the longitudinal connecting member in the sagittal plane or to hold the connecting member in place. Pressure pads for deformable rods may also be made from a deformable plastic material.

6 Claims, 20 Drawing Sheets

(56) References Cited

U.S. PATENT DOCUMENTS

| | | | |
|---|---|---|---|
| 2,531,892 A | 11/1950 | Reese | |
| 2,813,450 A | 11/1957 | Dzus | |
| 3,013,244 A | 12/1961 | Rudy | |
| 4,033,139 A | 7/1977 | Frederick | |
| 4,759,672 A | 7/1988 | Nilsen et al. | |
| 4,790,297 A | 12/1988 | Luque | |
| 4,946,458 A | 8/1990 | Harms et al. | |
| 5,019,080 A | 5/1991 | Hemer | |
| 5,129,388 A | 7/1992 | Vignaud et al. | |
| 5,176,680 A * | 1/1993 | Vignaud et al. | 606/302 |
| 5,207,678 A | 5/1993 | Harms et al. | |
| 5,261,912 A | 11/1993 | Frigg | |
| 5,312,404 A | 5/1994 | Asher et al. | |
| 5,360,431 A | 11/1994 | Puno et al. | |
| 5,395,371 A | 3/1995 | Miller et al. | |
| 5,429,639 A | 7/1995 | Judet | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,496,321 A | 3/1996 | Puno et al. | |
| 5,554,157 A | 9/1996 | Errico et al. | |
| 5,569,247 A | 10/1996 | Morrison | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,607,426 A | 3/1997 | Ralph et al. | |
| 5,647,873 A | 7/1997 | Errico et al. | |
| 5,669,911 A | 9/1997 | Errico et al. | |
| 5,672,176 A | 9/1997 | Biedermann et al. | |
| 5,681,319 A | 10/1997 | Biedermann et al. | |
| 5,690,630 A | 11/1997 | Errico et al. | |
| 5,716,356 A | 2/1998 | Biedermann et al. | |
| 5,725,528 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,782,833 A | 7/1998 | Haider | |
| 5,797,911 A | 8/1998 | Sherman et al. | |
| 5,800,435 A | 9/1998 | Errico et al. | |
| 5,817,094 A | 10/1998 | Errico et al. | |
| 5,863,293 A | 1/1999 | Richelsoph | |
| 5,873,878 A | 2/1999 | Harms et al. | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,938,663 A | 8/1999 | Petreto | |
| 5,954,725 A | 9/1999 | Sherman et al. | |
| 5,961,517 A | 10/1999 | Biedermann et al. | |
| 5,964,760 A | 10/1999 | Richelsoph | |
| 6,010,503 A | 1/2000 | Richelsoph et al. | |
| 6,019,759 A | 2/2000 | Rogozinski | |
| 6,022,350 A | 2/2000 | Ganem | |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Saurat | |
| 6,110,172 A | 8/2000 | Jackson | |
| 6,113,601 A | 9/2000 | Tatar | |
| 6,132,431 A | 10/2000 | Nilsson et al. | |
| 6,132,432 A | 10/2000 | Richelsoph | |
| 6,132,434 A | 10/2000 | Sherman et al. | |
| 6,146,383 A | 11/2000 | Studer et al. | |
| 6,183,472 B1 | 2/2001 | Lutz | |
| 6,186,718 B1 | 2/2001 | Fogard | |
| 6,187,005 B1 | 2/2001 | Brace et al. | |
| 6,214,012 B1 | 4/2001 | Karpman et al. | |
| RE37,161 E | 5/2001 | Michelson et al. | |
| 6,224,596 B1 | 5/2001 | Jackson | |
| 6,248,105 B1 | 6/2001 | Schlapfer et al. | |
| 6,254,602 B1 | 7/2001 | Justis | |
| 6,273,888 B1 | 8/2001 | Justis | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,296,642 B1 | 10/2001 | Morrison et al. | |
| 6,302,888 B1 | 10/2001 | Mellinger et al. | |
| 6,309,391 B1 | 10/2001 | Crandall et al. | |
| 6,331,179 B1 | 12/2001 | Freid et al. | |
| 6,355,040 B1 | 3/2002 | Richelsoph et al. | |
| RE37,665 E | 4/2002 | Ralph et al. | |
| 6,368,321 B1 | 4/2002 | Jackson | |
| 6,371,957 B1 | 4/2002 | Amrein et al. | |
| 6,402,752 B2 | 6/2002 | Schaffler-Wachter et al. | |
| 6,440,137 B1 | 8/2002 | Horvath et al. | |
| 6,451,021 B1 | 9/2002 | Ralph et al. | |
| 6,471,703 B1 | 10/2002 | Ashman | |
| 6,471,705 B1 | 10/2002 | Biedermann et al. | |
| 6,485,494 B1 | 11/2002 | Haider | |
| 6,488,681 B2 | 12/2002 | Martin et al. | |
| 6,508,818 B2 | 1/2003 | Steiner et al. | |
| 6,520,962 B1 | 2/2003 | Taylor et al. | |
| 6,527,804 B1 | 3/2003 | Gauchet et al. | |
| 6,530,929 B1 | 3/2003 | Justis et al. | |
| 6,533,786 B1 | 3/2003 | Needham et al. | |
| 6,547,790 B2 | 4/2003 | Harkey, III et al. | |
| 6,551,320 B2 | 4/2003 | Liebermann | |
| 6,554,832 B2 | 4/2003 | Shluzas | |
| 6,554,834 B1 | 4/2003 | Crozet et al. | |
| 6,558,387 B2 | 5/2003 | Errico et al. | |
| 6,562,040 B1 | 5/2003 | Wagner | |
| 6,565,565 B1 | 5/2003 | Yuan et al. | |
| 6,565,567 B1 | 5/2003 | Haider | |
| 6,582,436 B2 | 6/2003 | Schlapfer et al. | |
| 6,582,466 B1 | 6/2003 | Gauchet | |
| 6,585,740 B2 | 7/2003 | Schlapfer et al. | |
| 6,595,992 B1 | 7/2003 | Wagner et al. | |
| 6,595,993 B2 | 7/2003 | Donno et al. | |
| 6,610,063 B2 | 8/2003 | Kumar et al. | |
| 6,613,050 B1 | 9/2003 | Wagner et al. | |
| 6,623,485 B2 | 9/2003 | Doubler et al. | |
| 6,626,907 B2 | 9/2003 | Campbell et al. | |
| 6,626,908 B2 | 9/2003 | Cooper et al. | |
| 6,635,059 B2 | 10/2003 | Randall et al. | |
| 6,648,885 B1 | 11/2003 | Friesem | |
| 6,648,887 B2 | 11/2003 | Ashman | |
| 6,652,526 B1 | 11/2003 | Arafiles | |
| 6,656,179 B1 | 12/2003 | Schaefer et al. | |
| 6,656,181 B2 | 12/2003 | Dixon et al. | |
| 6,660,004 B2 | 12/2003 | Barker et al. | |
| 6,663,632 B1 | 12/2003 | Frigg | |
| 6,663,635 B2 | 12/2003 | Frigg et al. | |
| 6,673,073 B1 | 1/2004 | Schafer | |
| 6,676,661 B1 | 1/2004 | Benlloch et al. | |
| 6,679,833 B2 | 1/2004 | Smith et al. | |
| 6,682,529 B2 | 1/2004 | Stahurski | |
| 6,689,133 B2 | 2/2004 | Morrison et al. | |
| 6,689,134 B2 | 2/2004 | Ralph et al. | |
| 6,695,843 B2 | 2/2004 | Biedermann et al. | |
| 6,695,851 B2 | 2/2004 | Zdeblick et al. | |
| 6,699,249 B2 | 3/2004 | Schlapfer et al. | |
| 6,706,045 B2 | 3/2004 | Lin et al. | |
| 6,712,818 B1 | 3/2004 | Michelson | |
| 6,716,213 B2 | 4/2004 | Shitoto | |
| 6,716,214 B1 | 4/2004 | Jackson | |
| 6,716,247 B2 | 4/2004 | Michelson | |
| 6,723,100 B2 | 4/2004 | Biedermann et al. | |
| 6,730,093 B2 | 5/2004 | Saint Martin | |
| 6,730,127 B2 | 5/2004 | Michelson | |
| 6,733,502 B2 | 5/2004 | Altarac et al. | |
| 6,736,816 B2 | 5/2004 | Ritland | |
| 6,736,820 B2 | 5/2004 | Biedermann et al. | |
| 6,740,086 B2 | 5/2004 | Richelsoph | |
| 6,746,449 B2 | 6/2004 | Jones et al. | |

(56) References Cited

U.S. PATENT DOCUMENTS

| | | | |
|---|---|---|---|
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 6,932,817 B2 | 8/2005 | Baynham et al. |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mujwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,625,396 B2 * | 12/2009 | Jackson ..................... 606/305 |
| 7,641,674 B2 | 1/2010 | Young |
| 7,645,294 B2 | 1/2010 | Kalfasetd |
| 7,648,522 B2 | 1/2010 | David |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 * | 4/2010 | Landry et al. ............... 606/279 |
| 7,695,497 B2 | 4/2010 | Cordaro et al. |
| 7,695,498 B2 | 4/2010 | Ritland |
| 7,722,651 B2 * | 5/2010 | Kwak et al. .................. 606/265 |
| 7,862,588 B2 * | 1/2011 | Abdou ........................ 606/246 |
| 7,875,065 B2 * | 1/2011 | Jackson ....................... 606/305 |
| 7,947,065 B2 * | 5/2011 | Hammill et al. ............. 606/267 |
| 7,967,849 B2 * | 6/2011 | Carson et al. ............... 606/267 |
| 8,016,866 B2 * | 9/2011 | Warnick ...................... 606/305 |
| 8,308,782 B2 * | 11/2012 | Jackson ...................... 606/308 |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |

(56) References Cited

U.S. PATENT DOCUMENTS

| | | |
|---|---|---|
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Beidermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Beidermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079899 A1 | 4/2006 | Ritland |
| 2006/0084981 A1 | 4/2006 | Shluzas |
| 2006/0084989 A1 | 4/2006 | Dickinson et al. |
| 2006/0084993 A1 | 4/2006 | Landry et al. |
| 2006/0084995 A1 | 4/2006 | Biedermann et al. |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106383 A1 | 5/2006 | Biedermann et al. |
| 2006/0116677 A1 | 6/2006 | Burd et al. |
| 2006/0129147 A1 | 6/2006 | Biedermann et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfiled et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0195098 A1 | 8/2006 | Schumacher |
| 2006/0200128 A1 | 9/2006 | Mueller |
| 2006/0200131 A1 | 9/2006 | Chao et al. |
| 2006/0200149 A1 | 9/2006 | Hoy et al. |
| 2006/0212034 A1 | 9/2006 | Triplett et al. |
| 2006/0217716 A1 | 9/2006 | Baker et al. |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieznski et al. |
| 2006/0241600 A1 | 10/2006 | Ensign et al. |
| 2006/0247624 A1 | 11/2006 | Banouskou et al. |
| 2006/0247631 A1 | 11/2006 | Ahn et al. |
| 2006/0247636 A1 | 11/2006 | Yuan et al. |
| 2006/0247779 A1 | 11/2006 | Gordon et al. |
| 2006/0264933 A1 | 11/2006 | Baker et al. |
| 2006/0264936 A1 | 11/2006 | Partin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0293659 A1 | 12/2006 | Alvarez |
| 2006/0293665 A1 | 12/2006 | Shluzas |
| 2006/0293666 A1 | 12/2006 | Matthis et al. |
| 2007/0016188 A1 | 1/2007 | Boehm, Jr. et al. |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0055235 A1 | 3/2007 | Janowski et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123867 A1 | 5/2007 | Kirschman |
| 2007/0123870 A1 | 5/2007 | Jeon et al. |
| 2007/0161986 A1 | 7/2007 | Levy |

(56) References Cited

U.S. PATENT DOCUMENTS

| | | |
|---|---|---|
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173819 A1 | 7/2007 | Sandlin |
| 2007/0173820 A1 | 7/2007 | Trieu |
| 2007/0173828 A1 | 7/2007 | Firkins et al. |
| 2007/0191839 A1 | 8/2007 | Justis et al. |
| 2007/0198014 A1 | 8/2007 | Graf et al. |
| 2007/0208344 A1 | 9/2007 | Young |
| 2007/0225707 A1 | 9/2007 | Wisnewski et al. |
| 2007/0225711 A1 | 9/2007 | Ensign |
| 2007/0233078 A1 | 10/2007 | Justis et al. |
| 2007/0233080 A1 | 10/2007 | Na et al. |
| 2007/0233086 A1 | 10/2007 | Harms et al. |
| 2007/0233087 A1 | 10/2007 | Schlapfer |
| 2007/0250061 A1 | 10/2007 | Chin et al. |
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270815 A1 | 11/2007 | Johnson et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270839 A1 | 11/2007 | Jeon et al. |
| 2007/0288004 A1 | 12/2007 | Alvarez |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021473 A1 | 1/2008 | Butler et al. |
| 2008/0027432 A1 | 1/2008 | Strauss et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0058811 A1 | 3/2008 | Alleyne et al. |
| 2008/0058812 A1 | 3/2008 | Zehnder |
| 2008/0065073 A1 | 3/2008 | Perriello et al. |
| 2008/0065075 A1 | 3/2008 | Dant |
| 2008/0065077 A1 | 3/2008 | Ferree |
| 2008/0071273 A1 | 3/2008 | Hawkes et al. |
| 2008/0071274 A1 | 3/2008 | Enisgn |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0140075 A1 | 6/2008 | Ensign et al. |
| 2008/0161859 A1 | 7/2008 | Nilsson |
| 2008/0161863 A1 | 7/2008 | Arnold et al. |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0195159 A1 | 8/2008 | Kloss et al. |
| 2008/0200956 A1 | 8/2008 | Beckwith et al. |
| 2008/0215095 A1 | 9/2008 | Biedermann et al. |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0249570 A1 | 10/2008 | Carson et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1 | 10/2008 | Garamszegi |
| 2008/0287994 A1 | 11/2008 | Perez-Cruet et al. |
| 2008/0288002 A1 | 11/2008 | Crall et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Batters et al. |
| 2008/0312701 A1 | 12/2008 | Batters et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |

(56) References Cited

U.S. PATENT DOCUMENTS

| | | |
|---|---|---|
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0057125 A1 | 3/2010 | Viker |
| 2010/0057126 A1 | 3/2010 | Hestad |
| 2010/0063545 A1 | 3/2010 | Richelsoph |
| 2010/0063546 A1 | 3/2010 | Miller et al. |
| 2010/0063550 A1 | 3/2010 | Felix et al. |
| 2010/0063551 A1 | 3/2010 | Richelsoph |
| 2010/0069963 A1 | 3/2010 | Eckman |
| 2010/0069969 A1 | 3/2010 | Ampuero et al. |
| 2010/0087861 A1 | 4/2010 | Lechmann et al. |
| 2010/0087865 A1 | 4/2010 | Biedermann et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |

FOREIGN PATENT DOCUMENTS

| | | |
|---|---|---|
| EP | 1190678 | 3/2002 |
| EP | 1570795 | 9/2005 |
| EP | 1579816 | 9/2005 |
| EP | 1634537 | 3/2006 |
| EP | 1925263 | 5/2008 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 9202745.8 | 4/1992 |
| GB | 2365345 | 2/2002 |
| WO | WO95/01132 | 1/1995 |
| WO | WO02/054966 | 7/2002 |
| WO | WO03/068088 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |

OTHER PUBLICATIONS

*Claris Instrumentation* Brochure, G Med, pub. 1997.
*VLS System Variable Locking Screw* Brochure, Interpore Cross International, 1999.
*The Rod Plate System* Brochure, Stryker Howmedica Osteonics, pub. Oct. 1999.
*SDRS Surgical Dynamics Rod System* Brochure, Surgical Dynamics, pub. 1998-99.
*Versalok Low Back Fixation System* Brochure, Wright Medical Technology, Inc., pub. 1997.

\* cited by examiner

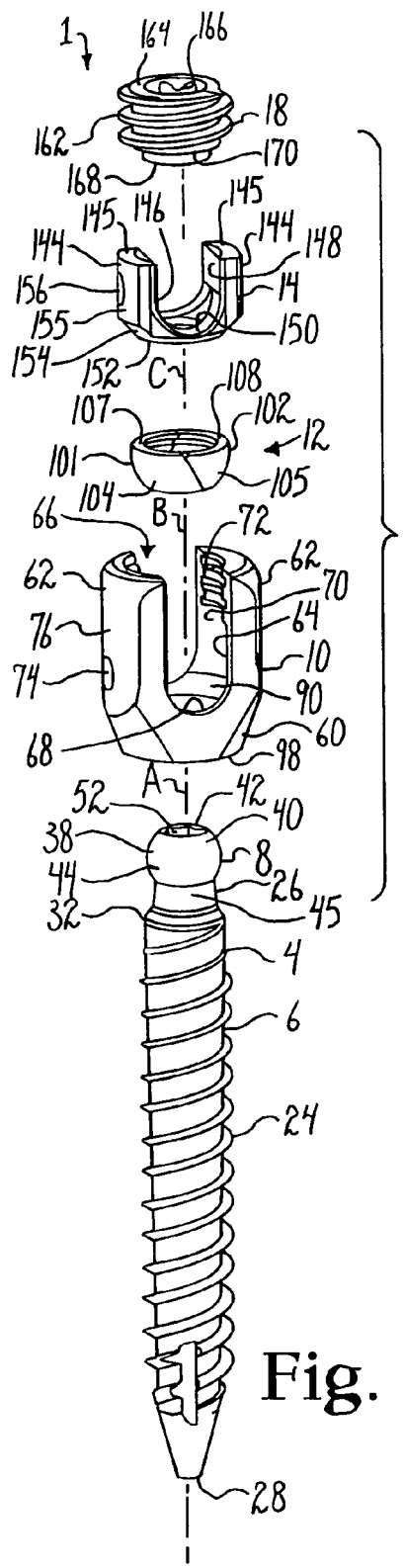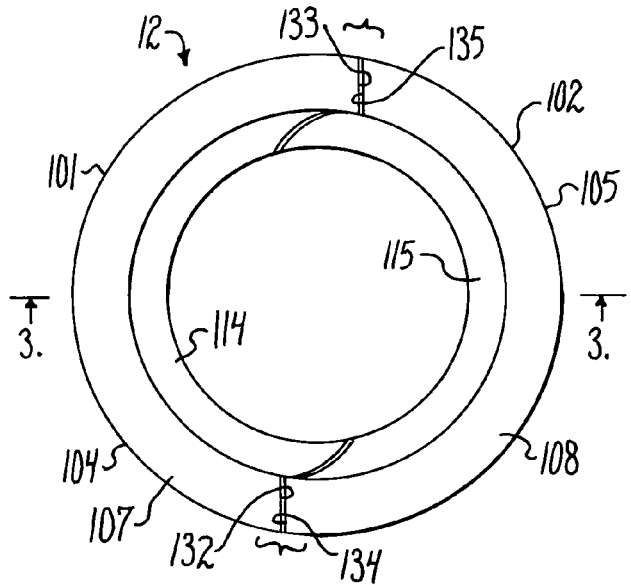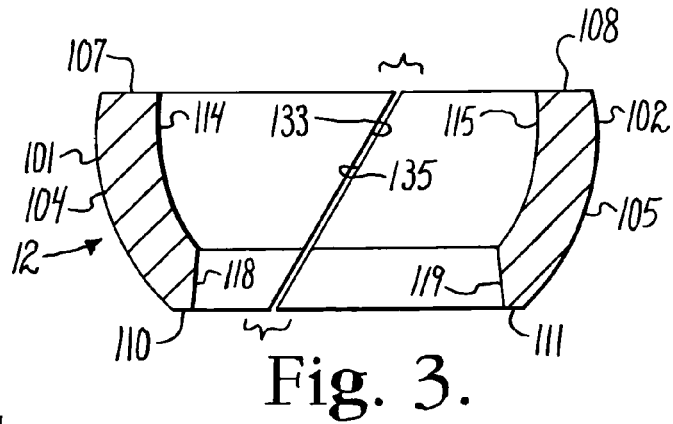
Fig. 1.
Fig. 2.
Fig. 3.

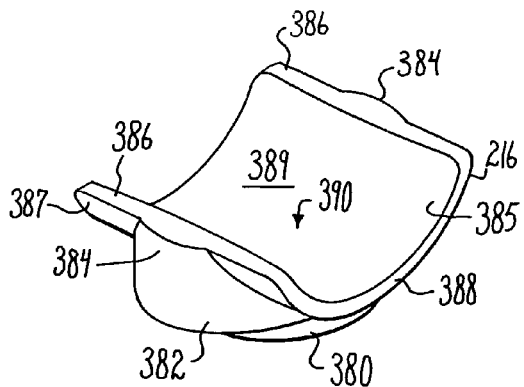
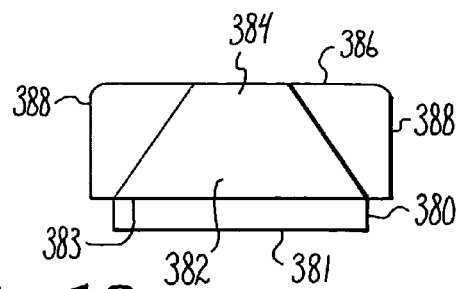
Fig. 16.
Fig. 18.
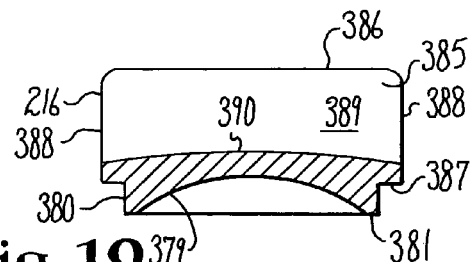
Fig. 19.
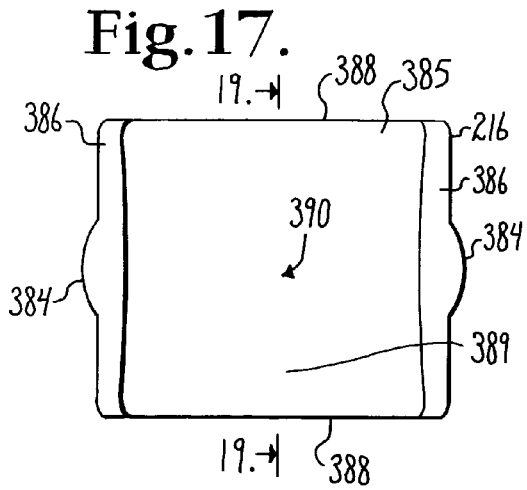
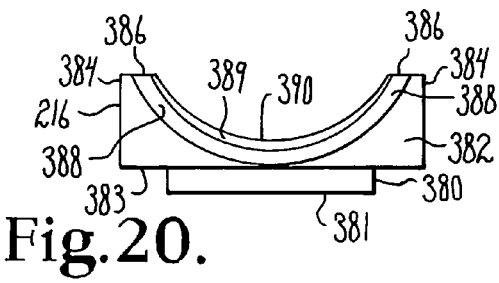
Fig. 17.
Fig. 20.
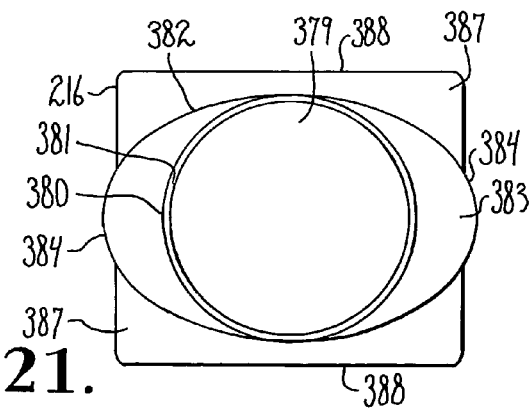
Fig. 21.

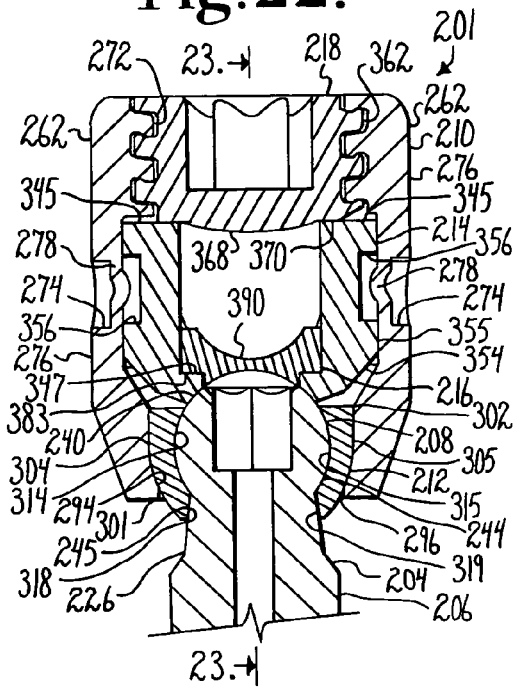
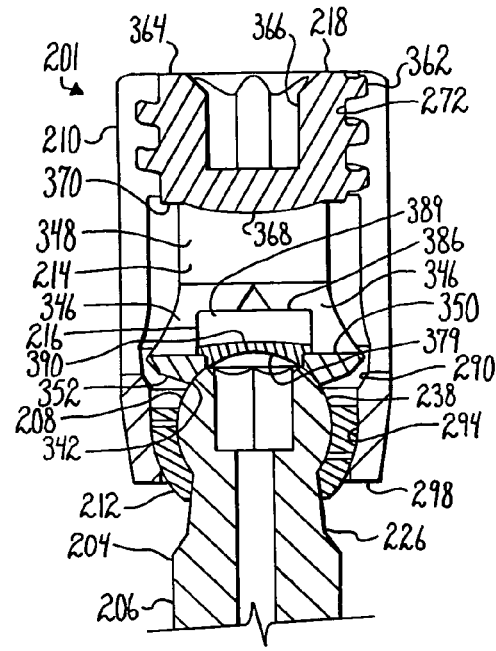
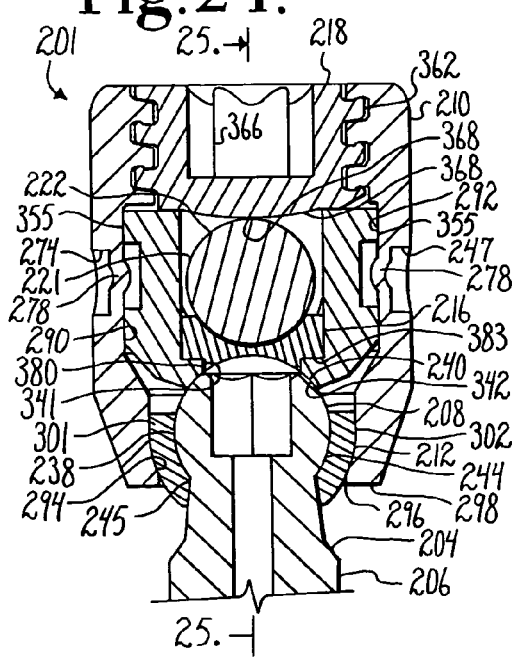
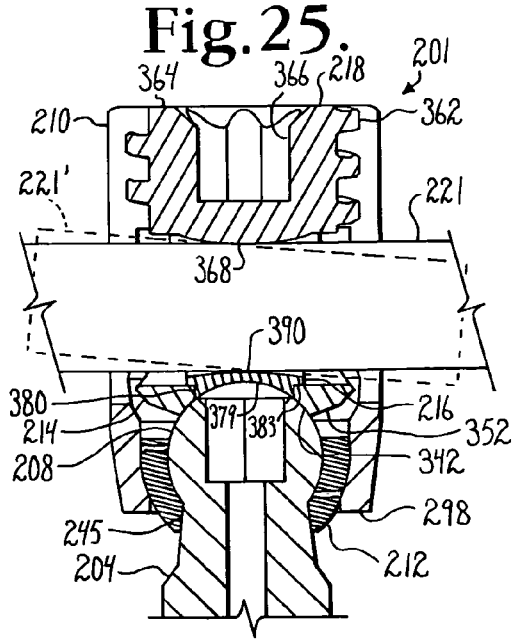

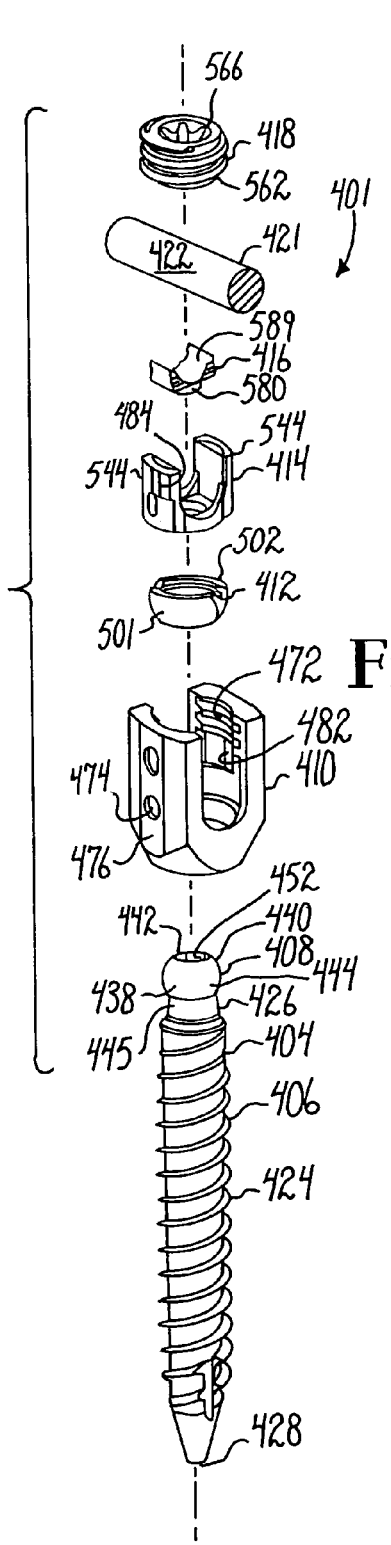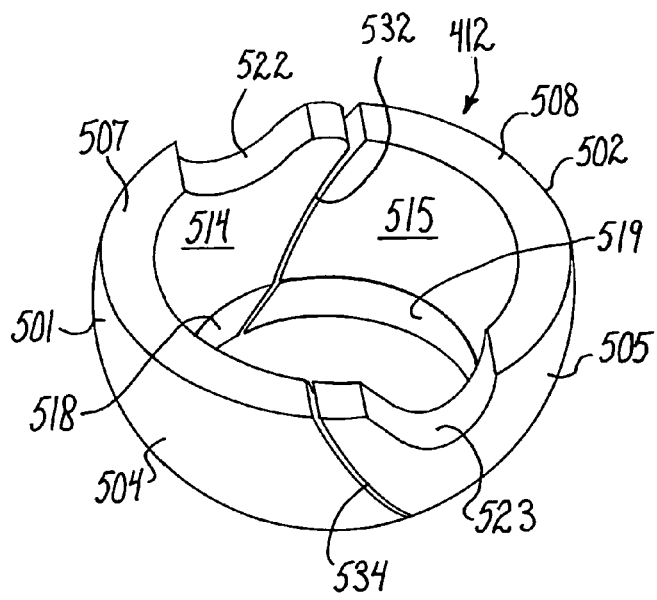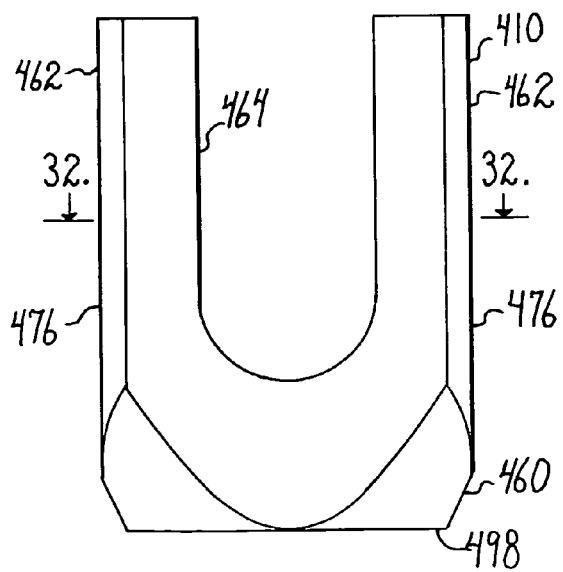
Fig. 28.
Fig. 29.
Fig. 30.

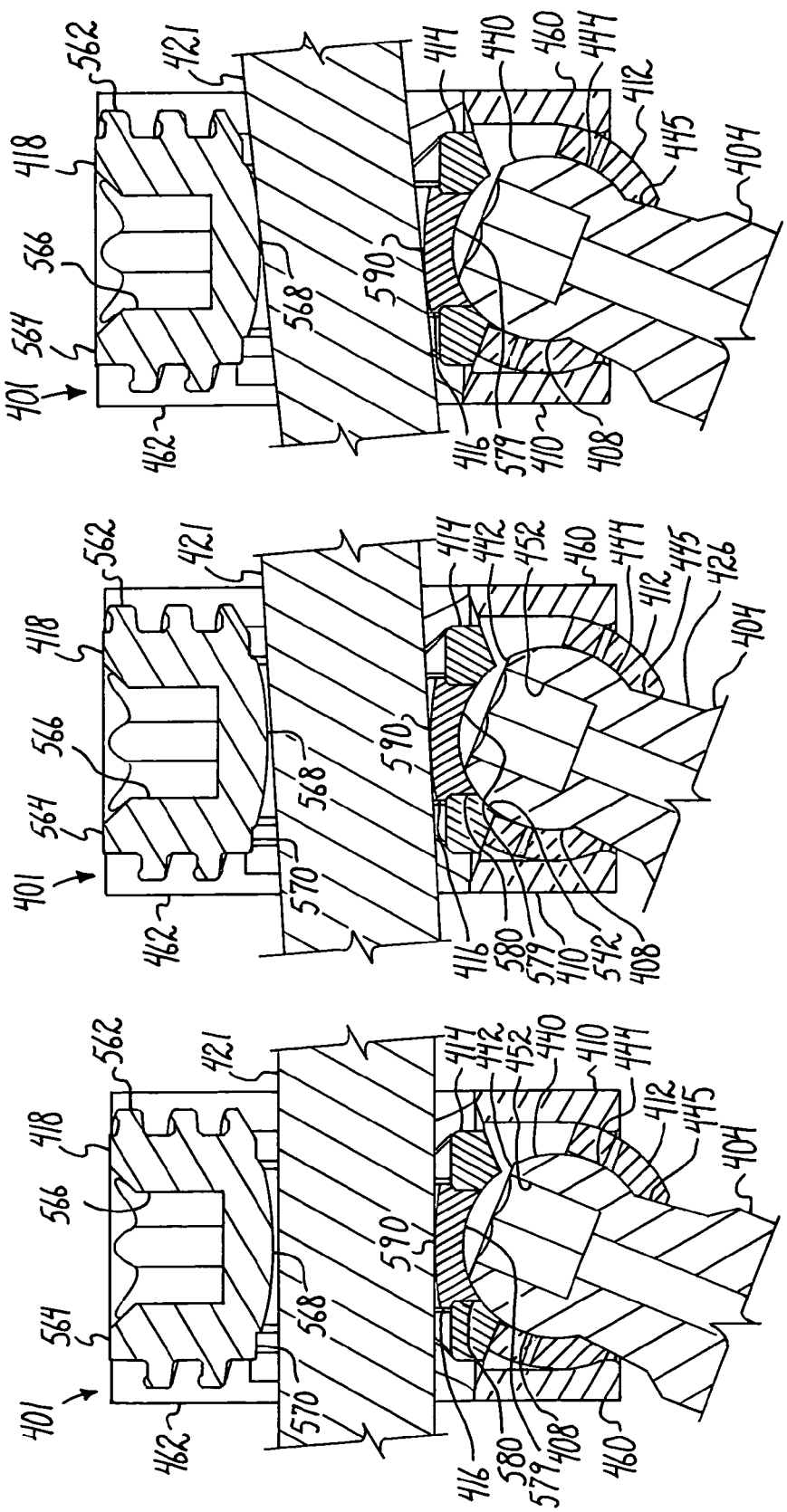

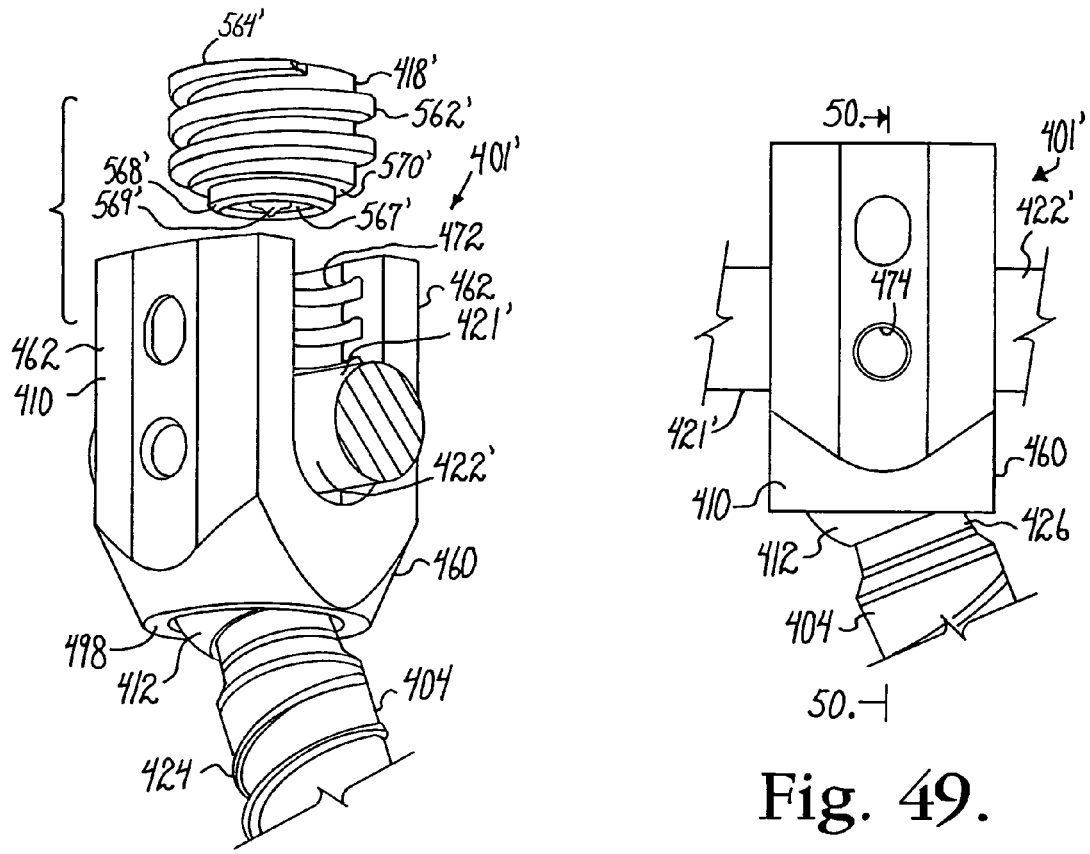
Fig. 48.
Fig. 49.
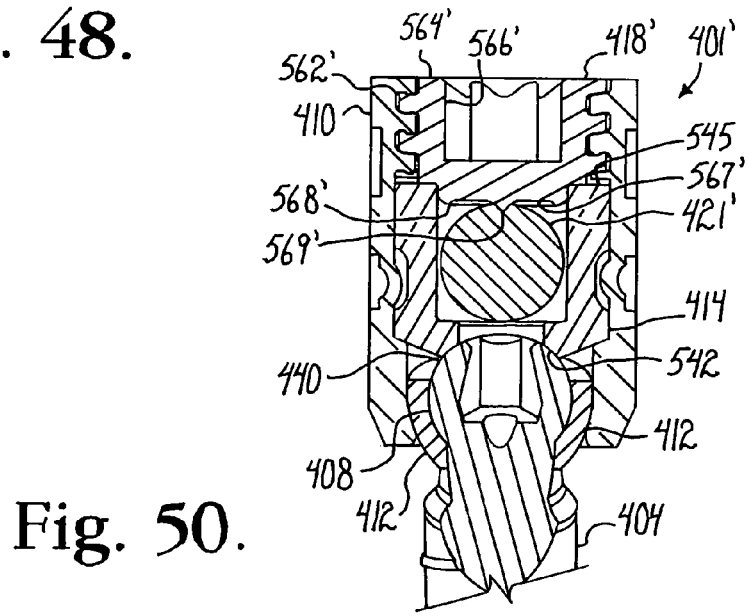
Fig. 50.

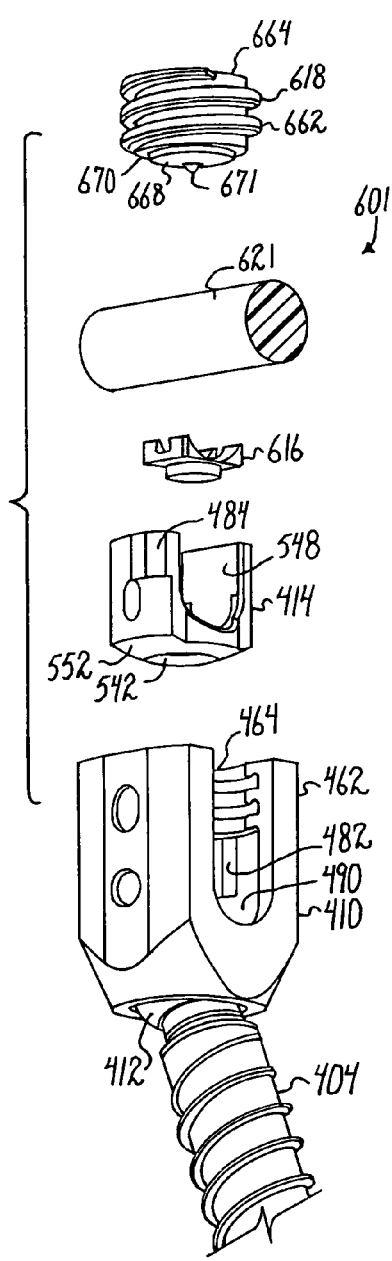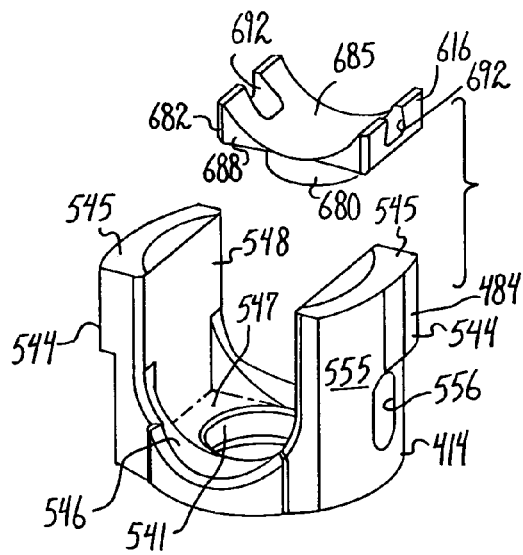
Fig. 52.
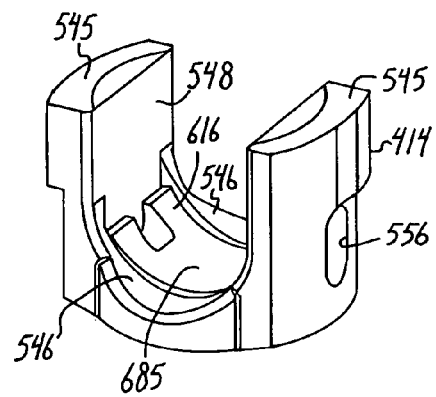
Fig. 51.
Fig. 53.

BONE ANCHORS WITH LONGITUDINAL CONNECTING MEMBER ENGAGING INSERTS AND CLOSURES FOR FIXATION AND OPTIONAL ANGULATION

CROSS-REFERENCE TO RELATED APPLICATIONS

This application is a continuation of U.S. patent application Ser. No. 12/804,999, filed Aug. 3, 2012 which claimed the benefit of U.S. Provisional Patent Application Ser. No. 61/273,399, filed Aug. 4, 2009, the disclosure of both of which are incorporated by reference herein. U.S. patent application Ser. No. 12/804,999 was also a continuation-in-part of U.S. patent application Ser. No. 12/080,202 filed Apr. 1, 2008 that is a continuation-in-part of U.S. patent application Ser. No. 11/281,818 filed Nov. 17, 2005, now U.S. Pat. No. 7,625,396, that claims the benefit of U.S. Provisional Patent Application Ser. No. 60/630,478 filed Nov. 23, 2004, all of the disclosures of which are incorporated by reference herein. U.S. patent application Ser. No. 12/804,999 was also a continuation-in-part of U.S. patent application Ser. No. 12/229,207 filed Aug. 20, 2008 that claims the benefit of U.S. Provisional Patent Application Ser. No. 60/994,083 filed Sep. 17, 2007 and was a continuation-in-part of U.S. patent application Ser. No. 11/522,503 filed Sep. 14, 2006 that is a continuation-in-part of U.S. patent application Ser. No. 11/024,543 filed Dec. 20, 2004, now U.S. Pat. No. 7,204,838, all of the disclosures of which are incorporated by reference herein.

BACKGROUND OF THE INVENTION

The present invention is directed to polyaxial bone screws for use in bone surgery, particularly spinal surgery and particularly to such screws that have pressure inserts.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod can be inserted into the head or receiver and eventually the receiver is locked or fixed in a particular position relative to the shank. During the rod implantation process it is desirable to utilize bone screws or other bone anchors that have components, or inserts that remain within the bone screw and further remain properly aligned during what is sometimes a very lengthy, difficult procedure.

SUMMARY OF THE INVENTION

A polyaxial bone screw assembly according to the invention includes a shank having an upper portion and a body for fixation to a bone; a head or receiver defining an open channel; a multi-part or piece retainer for pivotally holding the upper portion in the receiver; and at least one compression insert spaced above and apart from the retainer structure. The shank upper portion is bottom or up-loadable into the receiver, cooperates with the retainer, and has a top end which extends above a top surface of the retainer, the retainer having polyaxial motion with respect to the receiver, and the retainer including more than one discrete piece, each piece frictionally engageable with the shank upper portion, slidably engageable with the receiver and located between the shank upper portion and the receiver and spaced below the insert. The compression insert includes arms defining a U-shaped channel for receiving a longitudinal connecting member, the arms preferably extending upwardly beyond a periphery of the connecting member being received within the U-shaped channel. In some embodiments, the compression insert arms directly engage a closure top to lock the polyaxial mechanism of the screw while capturing but not necessarily locking the longitudinal connecting member within the receiver. In other embodiments, an alternative closure top directly engages a longitudinal connecting member that in turn engages the lower pressure insert, pressing the insert into frictional engagement with the upper portion of the bone screw shank to lock the polyaxial mechanism and fix the longitudinal connecting member with respect to the screw.

An alternative embodiment of a polyaxial screw according to the invention includes an insert and closure top combination that provides for some sagittal plane angulation of a longitudinal connecting member being held by the screw. The insert and closure top each include convex or domed shaped surfaces facing the longitudinal connecting member. The domed surface of the closure top may be integral with or otherwise attached to a remainder of the closure top.

Other alternative polyaxial and mono-axial bone screws according to the invention include a deformable insert for closely engaging a connecting member that may be hard or of a deformable or elastic material.

It is an object of the invention to provide apparatus and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged exploded perspective view of a polyaxial bone screw assembly according to the present invention including a shank, a receiver, a retainer having two discreet pieces, a compression insert and a closure top.

FIG. 2 is an enlarged top plan view of the two-piece retainer of FIG. 1.

FIG. 3 is an enlarged cross-sectional view taken along the line 3-3 of FIG. 2.

FIG. 16 is an enlarged perspective view of the pivot insert of FIG. 15.

FIG. 17 is an enlarged top plan view of the pivot insert of FIG. 15.

FIG. 18 is an enlarged side elevational view of the pivot insert of FIG. 15.

FIG. 19 is a cross-sectional view taken along the line 19-19 of FIG. 17.

FIG. 20 is an enlarged front elevational view of the pivot insert of FIG. 15.

FIG. 21 is an enlarged bottom plan view of the pivot insert of FIG. 15.

FIG. 22 is an enlarged and partial front elevational view of the assembly of FIG. 15, with portions broken away to show the detail thereof, shown fully assembled without the longitudinal connecting member.

FIG. 23 is an enlarged and partial cross-sectional view taken along the line 23-23 of FIG. 22.

FIG. 24 is an enlarged and partial front elevational view of the assembly of FIG. 15, with portions broken away to show the detail thereof and shown fully assembled with the longitudinal connecting member.

FIG. 25 is an enlarged and partial cross-sectional view taken along the line 25-25 of FIG. 24 and showing a degree of angulation of the longitudinal connecting member in phantom.

FIG. 28 is an enlarged and partial exploded perspective view of a third, alternative embodiment of a polyaxial bone screw assembly according to the present invention including a shank, a receiver, a retainer having two discreet pieces, a compression insert, a pivot insert, and a closure top, and further shown with a longitudinal connecting member in the form of a rod.

FIG. 29 is an enlarged perspective view of the two piece retainer of FIG. 28.

FIG. 30 is an enlarged front elevational view of the receiver of FIG. 28.

FIG. 45 is an enlarged and partial side elevational view of the assembly of FIG. 43 with portions broken away to show the detail thereof and shown with zero degree rod toggle.

FIG. 46 is an enlarged and partial side elevational view of the assembly of FIG. 43 with portions broken away to show the detail thereof and shown with three degree rod toggle.

FIG. 47 is an enlarged and partial side elevational view of the assembly of FIG. 43 with portions broken away to show the detail thereof and shown with six degree rod toggle.

FIG. 48 is an enlarged and partial and partially exploded perspective view of the bone screw assembly of FIG. 28 shown with an alternative closure top.

FIG. 49 is an enlarged and partial side elevational view of the assembly of FIG. 48.

FIG. 50 is an enlarged and partial cross-sectional view taken along the line 50-50 of FIG. 49.

FIG. 51 is an enlarged and partial, partially exploded perspective view of a fourth, alternative embodiment of a polyaxial bone screw assembly according to the present invention including a shank, a receiver, a retainer having two discreet pieces, a compression insert, a connecting member support insert, and a closure top, and further shown with a longitudinal connecting member in the form of a deformable rod.

FIG. 52 is an enlarged exploded perspective view of the compression insert and support insert of FIG. 51.

FIG. 53 is an enlarged perspective view, similar to FIG. 52, showing the compression insert and support insert assembled.

DETAILED DESCRIPTION OF THE INVENTION

Figure 4:
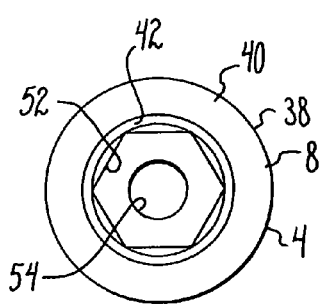
FIG. 4 is an enlarged and partial top plan view of the shank of FIG. 1.
Figure 5:
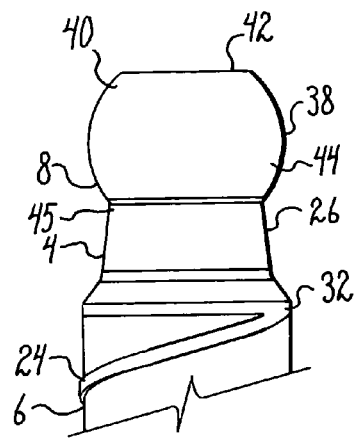
FIG. 5 is an enlarged and partial front elevational view of the shank of FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-14 the reference number 1 generally represents a polyaxial bone screw apparatus or assembly according to the present invention. The assembly 1 includes a shank 4, that further includes a body 6 integral with an upwardly extending upper portion or capture structure 8; a receiver 10; a retainer structure, generally 12, having two or more pieces; and a compression or pressure insert 14. The shank 4, receiver 10, retainer structure 12 pieces and pressure insert 14 preferably are assembled prior to implantation of the shank body 6 into a vertebra (not shown).

FIG. 1 further shows a closure structure 18 of the invention for capturing a longitudinal member such as a hard, inelastic rod 21 (shown, e.g., in FIG. 12) within the pressure insert 14 which in turn engages an upper curved area of the shank upper portion and biases the retainer structure 12 pieces into fixed frictional contact with both the shank upper portion 8 and the receiver 10, so as to capture, and in some embodiments, fix the longitudinal connecting member 21 within the receiver 10 and thus fix the member 21 relative to the vertebra. The illustrated rod 21 is hard, non-elastic and cylindrical, having an outer cylindrical surface 22. In other embodiments, the rod 21 may be deformable and/or of a different cross-sectional geometry, as will be described in greater detail below. The upper curved area of the shank upper portion 8 is spaced above the retainer 12 and the retainer 12 is disposed between the shank upper portion 8 and the receiver 10. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. In some embodiments, the shank upper portion 8 may further include a radially extending shelf, extension or resilient, compressible and/or split ring to aid in holding the retainer 12 pieces in a desired, fixed location with respect to the shank upper portion 8.

The shank 4, best illustrated in FIGS. 1-9, is elongate, with the shank body 6 having a helically wound bone implantable thread 24 (single or dual lead thread form) extending from near a neck 26 located adjacent to the upper portion or capture structure 8, to a tip 28 of the body 6 and extending radially outwardly therefrom. During use, the body 6 utilizing the thread 24 for gripping and advancement is implanted into a vertebra leading with the tip 28 and driven down into the vertebra with an installation or driving tool (not shown), so as to be implanted in the vertebra to near the neck 26, as more fully described in the paragraphs below. The shank 4 has an elongate axis of rotation generally identified by the reference letter A.

The neck 26 extends axially upward from the shank body 6. The neck 26 may be of slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the upper end 32 and thus at a distance from a vertebra when the body 6 is implanted in such vertebra.

The shank upper portion or capture structure 8 is configured for connecting the shank 4 to the receiver 10 and capturing the shank upper portion structure in the receiver 10. In the embodiment shown, the structure 8 has a substantially spherical body 38. An upper surface end portion 40 of the body 38 is adjacent to a planar annular top surface 42. The top surface 42 is disposed perpendicular to the axis A. It is foreseen that in other embodiments of the invention, the spherical body 38 may alternatively take the form of a polyhedral formation or other curved shape, such as, for example, cylindrical or conical. The upper surface portion 40 is substantially spherical and terminates at the narrow top annular surface 42. The portion 40 forms a partial dome near the surface 42 for closely engaging a spherical surface of the insert 14 as will be described in greater detail below. A lower surface portion 44 of the spherical body 38 extends from the upper surface portion 40 to the shank neck 26. The lower surface portion 44 and an adjacent portion 45 of the neck 26 closely engage inner surfaces of the retainer 12 pieces as will be described in greater detail below.

The shank 4 further includes a tool engagement structure or inner drive 52 formed in the top surface 42. The illustrated drive 52 is a hex drive or aperture for engaging a similarly shaped driving tool (not shown) for both driving and rotating the shank body 6 into a vertebra. Other shaped drives and cooperating tools are possible, such as grooved, multi-lobular, etc. While not required in accordance with the practice of the invention, the lower surface portion 44 and/or the upper surface 40 may be scored, threaded, ridged or knurled to further increase frictional engagement between such surfaces and respective cooperating surfaces of the retainer 12 and the insert 14.

The shank 4 shown in the drawings is cannulated, having a small central bore 54 extending an entire length of the shank 4 along the axis A from the internal drive 52 to the tip 28. The bore 54 is coaxial with the threaded body 6. The bore 54 provides a passage through the shank 4 interior for a length of wire (not shown) inserted into a vertebra prior to the insertion of the shank body 6, the wire providing a guide for insertion of the shank body 6 into the vertebra 15.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 6-9, the receiver 10 has a generally U-shaped appearance with a discontinuous partially cylindrical and partially spherical inner profile and a partially curved and partially faceted outer profile. The receiver 10 has an axis of rotation B that is shown in FIG. 1 as being aligned with and the same as the axis of rotation A of the shank 4, such orientation being desirable during assembly of the receiver 10 with the shank 4, the retainer pieces 12 and the insert 14. After the receiver 10 is pivotally attached to the shank 4, and the assembly 1 is implanted in a vertebra (not shown), the axis B is typically disposed at an angle with respect to the axis A.

The receiver 10 includes a base 60 integral with a pair of opposed upstanding arms 62 forming a cradle and defining a U-shaped channel 64 between the arms 62 with an upper opening, generally 66, and a lower seat 68, the channel 64 having a width for operably snugly receiving the rod 21 between the arms 62. Each of the arms 62 has an interior surface 70 that defines the inner cylindrical profile and includes a partial helically wound guide and advancement structure 72. In the illustrated embodiment, the guide and advancement structure 72 is a partial helically wound interlocking flange form configured to mate under rotation with a similar structure on the closure structure 18, as described more fully below. However, it is foreseen that the guide and advancement structure 72 could alternatively be a square-shaped thread, a buttress thread, a reverse angle thread or other thread-like or non-thread-like helically wound discontinuous advancement structure for operably guiding under rotation and advancing the closure structure 18 downward between the arms 62, as well as eventual torquing when the closure structure 18 abuts against the rod 21 in some embodiments or abuts against the compression insert 14 in other embodiments.

An opposed pair of tool receiving and engaging apertures 74 are formed on outer surfaces 76 of the arms 62. As illustrated, the apertures 74 do not extend completely through the arms 62. At each aperture 74, a thin wall 78 partially defines the aperture and may be crimped or pushed inwardly toward and into a cooperating aperture of the pressure insert 14 as will be described in greater detail below. Alternatively, the receiver 10 or the pressure insert 14 may be equipped with spring tabs that bias against a respective pressure insert or receiver to prohibit rotational movement of the insert 14 about the receiver axis B once the insert 14 is loaded in the receiver 10 and positioned with the rod-receiving channel of the insert 14 in alignment with the U-shaped channel 64 of the receiver.

Communicating with the U-shaped channel 64 of the receiver 10 is a chamber or cavity 90 defined in part by a substantially cylindrical upper portion 92, a substantially conical middle portion 93 and by a lower inner substantially spherical retainer seating surface 94 of the base 60. The upper portion 92 is located below the guide and advancement structures 72 and may include one or more cylindrical surfaces for sliding cooperation with an insert or inserts. The walls 78 defining the apertures 74 communicate with the cylindrical upper portion 92. The substantially conical mid-portion 93 is adjacent to the upper portion 92 near the seating surface 68 of the U-shaped channel 64. The mid-portion 93 is also adjacent to the seating surface 94. The seating surface 94 is sized and shaped for slidable mating and eventual frictional engagement with the retainer pieces 12, as described more fully below. The cavity 90 opens into the U-shaped channel 64 and also to a lower neck 96 defining a bore or circular opening that communicates with a lower exterior 98 of the base 60. The circular neck 96 is coaxially aligned with the rotational axis B of the receiver 10. The neck 96 is sized and shaped to be smaller than an outer radial dimension of the operationally assembled retainer pieces 12, as will be discussed further below, so as to form a restriction at the location of the neck relative to the retainer 12, to prevent the retainer 12 from passing from the cavity 90 and out to the lower exterior 98 of the receiver 10 when the retainer 12 is seated and assembled about the shank upper portion 8.

With particular reference to FIGS. 1-3 and 6-7, the two-part retainer 12 is used to retain the upper portion or capture structure 8 of the shank 4 within the receiver 10 and also articulate the shank body 6 with respect to the receiver 10. The retainer pieces are each sized and shaped to frictionally engage the shank upper portion while being pivotally mounted with respect to the receiver 10, the pieces located below the upper surface portion 40 and between the lower surface portion 44 and the receiver base 60 and being articulatable with respect to the receiver seating surface 94 until the shank 6 is fixed in a desired position with respect to the receiver base 60. The retainer structure 12, best illustrated in FIGS. 1-3, has an operational central axis C that is the same as the axis A associated with the shank 4. The structure 12 includes a first piece or part 101 and an oppositely positioned, and in this embodiment a substantially identical or mirror image second piece or part 102. The parts 101 and 102 provide a collar about the shank upper portion 8 and a portion of the shank neck 26, with the upper surface portion 40 extending upwardly above the parts 101 and 102 and towards the opening 66 within the receiver 10, and each of the parts 101 and 102 disposed between the portion 8 and the receiver 10 when installed, as will be discussed more fully below. Once installed and locked into position, the parts or pieces 101 and 102 closely grip both the shank 4 at the surfaces 44 and 45 and also the receiver seating surface 94, providing an even and uniform gripping surface between the shank 4 and the receiver 10 at the spherical seating surface 94 when force is directed onto the shank domed surface 40 by the insert 14 cooperating with the rod 21 and/or the closure structure 18, or by other types of longitudinal members, inserts and closure structures.

Although a two-piece retainer structure 12 is illustrated herein, it is foreseen that the retainer structure may be made up of more than two pieces, each frictionally matable with both the shank upper portion or capture structure 8 and the seating surface 94 of the receiver 10. The pieces may also be of varying sizes and not necessarily mirror images of one another. The mating surfaces of the shank upper portion and cooperating retainer pieces may further include planar surfaces that may be tapered or parallel or other curved surfaces, for example, cylindrical or conical in form. Additionally, it is foreseen that the pieces may include a plurality of planar or curved surfaces, such as undulating or zig-zag surfaces, forming peaks and valleys that would cooperate and mate with similarly configured surfaces on the shank upper portion. Furthermore, the parts 101 and 102 may be in frictional contact or spaced from one another when fully installed in the receiver 10 and in contact with the shank upper portion 8. The parts 101 and 102 can also be interlocking with each other or in some other way cooperating with each other and/or with the compression insert in the receiver cavity such that the shank may be uploaded into the receiver in a "snap-on" or "pop-on" fashion allowing the receiver and pre-loaded retainer pieces and compression insert to be assembled with the shank either at the factory, by surgical staff before implantation of the assembly 1, or after the shank alone is implanted into a vertebra.

Figure 8:
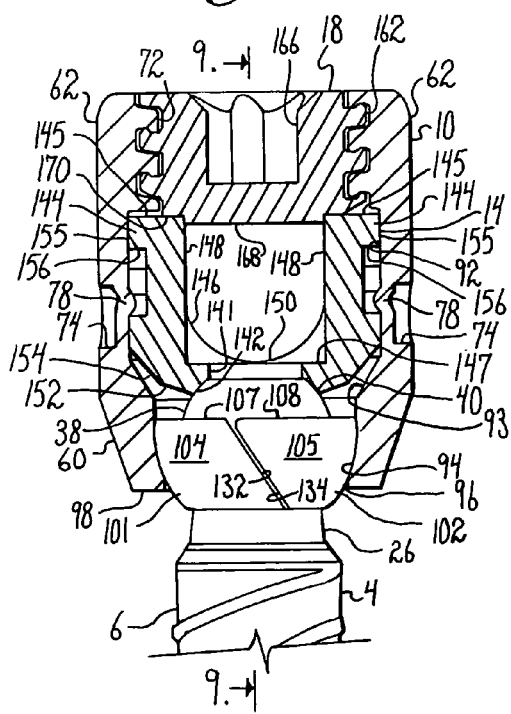
FIG. 8 is an enlarged and partial front elevational view of the shank retainer pieces, compression insert, receiver and closure top of FIG. 1, shown fully assembled (without a longitudinal connecting member), with portions broken away to show the detail thereof.
Figure 9:
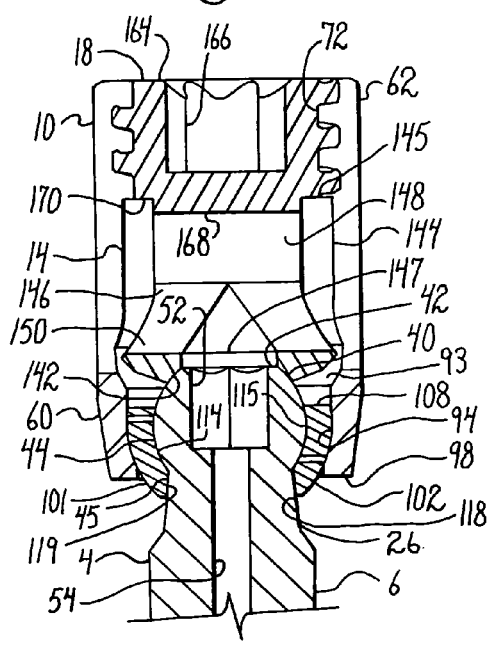
FIG. 9 is an enlarged and partial cross-sectional view taken along the line 9-9 of FIG. 8.

Each retainer part 101 and 102 includes a substantially spherical outer surface, 104 and 105, respectively, each having a radius substantially similar to a radius of the receiver seating surface 94. The parts 101 and 102 further include respective planar top surfaces 107 and 108 and respective planar bottom surfaces 110 and 111. The illustrated surface 107 and the surface 110 are substantially parallel. The illustrated surface 108 and the surface 111 are substantially parallel. Adjacent to the top surfaces 107 and 108 are respective substantially spherical inner surfaces 114 and 115. The surface 114 is adjacent to an inner frusto-conical surface 118 and the surface 115 is adjacent to an inner frusto-conical surface 119. The inner spherical surfaces 114 and 115 each have a radius identical or substantially similar to the radius of the shank upper portion body 38, being sized and shaped to closely frictionally mate with the lower surface 44 of the body 38. The frusto-conical surfaces 118 and 119 are sized and shaped to be closely, frictionally received about the shank neck 26 at the surface 45. As illustrated in FIG. 9, for example, the inner surfaces 114 and 115 and the outer spherical surfaces 104 and 105 are advantageously sized to allow for clearance between the retainer 12 and the insert 14 when pivoting the shank 4 with respect to the receiver 10 into a desired position. With particular reference to FIGS. 8-9, when the retainer structure parts 101 and 102 are operationally disposed in the receiver 10, the inner surfaces 118 and 119 are seated on the shank neck surface 45 and frictionally engaged thereto and the inner spherical surfaces 114 and 115 are frictionally gripping the shank body 38 at the surface 44, while the outer spherical surfaces 104 and 105 are free to slide with respect to the receiver seating surface 94 until locked into place by pressure from the closure 18 pressing on the insert 14 that in turn presses exclusively on the shank domed upper surface 40.

With particular reference to FIGS. 2 and 8, the retainer part or piece 101 further includes opposed end walls 132 and 133, extending from the outer surface 104 to the inner walls 114 and 118. The end walls 132 and 133 are disposed at an oblique angle to the respective top and bottom surfaces 107 and 110. The retainer part 102 further includes end walls 134 and 135, extending from the outer surface 105 to the inner walls 115 and 119. The end walls 134 and 135 are disposed at an oblique angle to the respective top and bottom surfaces 108 and 111. In some embodiments according to the invention, each of the walls 132, 133, 134 and 135 are oriented substantially perpendicular to the top and bottom surfaces of the respective retainer pieces. Angles other than what is illustrated may also be used. Each of the walls 132, 133, 134 and 135 may include beveled surfaces. The retainer parts 101 and 102 are configured such that, when operationally disposed in the receiver 10, with the substantially spherical surfaces 104 and 105 in sliding frictional contact with the spherical seating surface 94, and with the inner surfaces 118 and 119 seated on the frusto-conical neck surface 45 of the shank 4, the end walls 132 and 133 are closely spaced or in contact with the respective end walls 134 and 135, as illustrated in FIGS. 2, 3 and 8. It is foreseen that also in accordance with the invention, to provide additional clearance during installation, the illustrated parts 101 and 102 are configured such that the end walls 132 and 133 are in spaced, substantially parallel relation with the respective end walls 134 and 135, when fully installed in the bone screw receiver 10.

With particular reference to FIGS. 1 and 8-9, the illustrated compression insert 14 is sized and shaped to be received by and downloaded into the receiver 10 at the upper opening 66. However, in other embodiments of the invention, the insert 14 may be sized for uploading or downloading into the receiver 10. The compression insert 14 has an operational central axis that is the same as the central axis B of the receiver 10. The compression insert 14 has a central channel or through bore substantially defined by an inner cylindrical surface 141 coaxial with an inner partially spherical surface 142. The compression insert 14 through bore is sized and shaped to receive a driving tool (not shown) therethrough that engages the shank drive feature 52 when the shank body 6 is driven into bone. The surface 142 is sized and shaped to slidingly receive and ultimately frictionally engage the substantially spherical or domed surface 40 of the shank upper portion 8 such that the surface 142 initially slidingly and pivotally mates with the spherical surface 40. The surface 142 may include a roughening or surface finish to aid in frictional contact between the surface 142 and the surface 40, once a desired angle of articulation of the shank 4 with respect to the receiver 10 is reached.

The compression insert 14 also includes a pair of arms 144, each having a top surface 145, with a pair of U-shaped saddle-like surfaces 146 running between the arms and forming a seat for a longitudinal connecting member, such as the rod 21. A centrally located lower planar surface 147 is disposed between portions of the saddle-like surfaces 146, the planar surface 147 partially defining an opening of the central channel at the cylindrical surface 141. The planar surface 147 is disposed substantially perpendicular to the cylindrical surface 141. Portions of the saddle surfaces 146 also communicate with the bore defined by the cylindrical surface 141. The curved surfaces 146 are sized and shaped to closely receive the cylindrical rod 21 or other longitudinal connecting member. The saddle-like surfaces 146 extend between substantially planar opposed inner surfaces 148 of the arms 144, the inner surfaces 148 extending to the top surfaces 145 of the arms. The spaced saddle-like surfaces 146 form a lower seat 150 located near a lower or bottom surface 152 of the insert 14. The surface 152 slopes upwardly from and communicates with the inner spherical surface 142, the surface 152 allowing for clearance between the insert 14 and the retainer pieces 12 as best shown in FIG. 8. The arms 144 have a height dimension such that the top surfaces 145 are disposed above the rod 21 or other longitudinal connecting member captured by the assembly 1. The arms 144 preferably have an adequate thickness so that the arms 144 closely capture the rod 21 therebetween and also are supported by the cylindrical wall 92 defining the receiver cavity 90 directly under the guide and advancement structure 72.

In operation, the lower seat 150 (as well as at least a substantial portion of a remainder of the saddle 146) frictionally engages an outer surface 22 of the rod 21. A frusto-conical base outer surface 154 extends generally from the arms 144 to the bottom surface 152. The illustrated insert 14 is partially cylindrical and partially conical with the surface 154 sloping upwardly to outer surfaces 155 of the arms 144. Formed in the surfaces 155 and located centrally with respect to each arm 144 is a shallow groove or depression 156. Each illustrated groove 156 is substantially U-shaped and is sized and shaped to cooperate with the apertures 74 and receiver thin inner walls 78 as will be described in greater detail below. The grooves 156 may be of any shape and are preferably elongate, running parallel to a central axis of the insert 14 that is operationally coaxial with the axis B of the receiver 10. In some embodiments of the invention, the grooves or depressions 156 may be substantially flat surfaces formed by planing the cylindrical surface 155. The compression or pressure insert 14 ultimately seats on the shank upper portion 8 and is disposed substantially in the upper cylindrical portion 92 of the cavity 90, with the walls 78 being pressed or crimped into each depression 156 to hold the insert 14 in a desired alignment with respect to the rod 21 as will be described in greater detail below. In operation, the insert 14 extends at least partially in the channel 64 of the receiver 10 such that the saddle 146 surface substantially contacts and engages the outer surface 22 of the rod 21 when such rod is placed in the receiver 10 and the closure structure or top 18 is tightened thereon.

Figure 12:
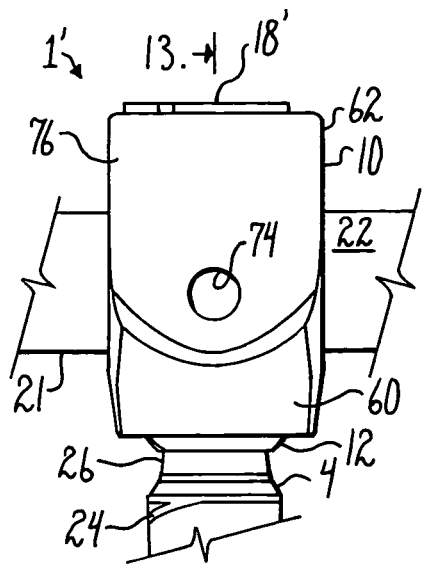
FIG. 12 is an enlarged and partial side elevational view of the assembly of FIG. 1 shown with the alternative closure top of FIG. 10 and a longitudinal connecting member.
Figure 11:
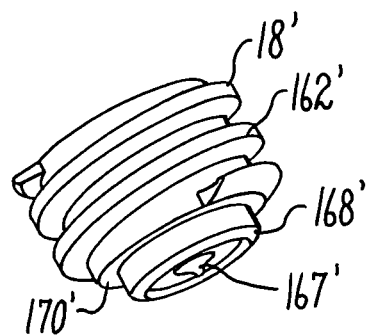
FIG. 11 is an enlarged perspective view of the alternative closure top of FIG. 10.
Figure 10:
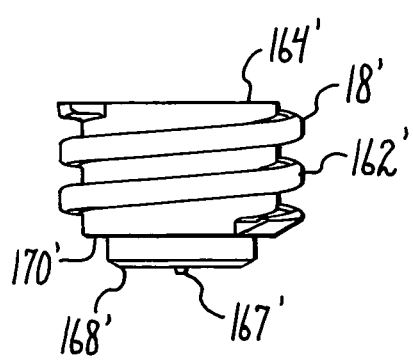
FIG. 10 is an enlarged front elevational view of an alternative closure top for use with the assembly of FIG. 1.
Figure 13:
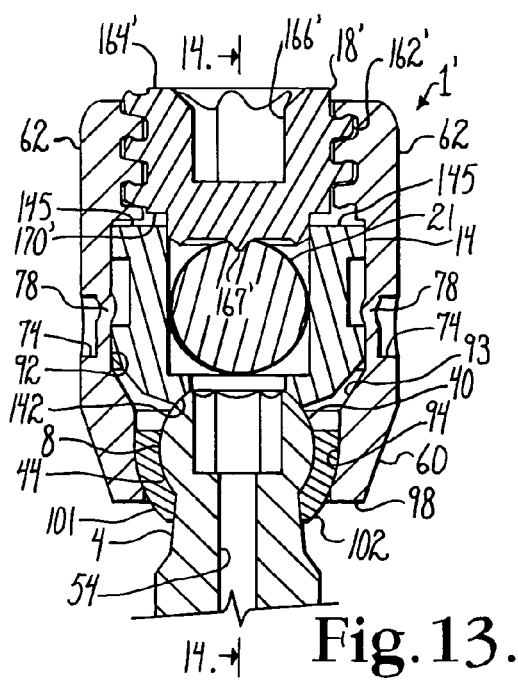
FIG. 13 is an enlarged and partial cross-sectional view taken along the line 13-13 of FIG. 12.
Figure 14:
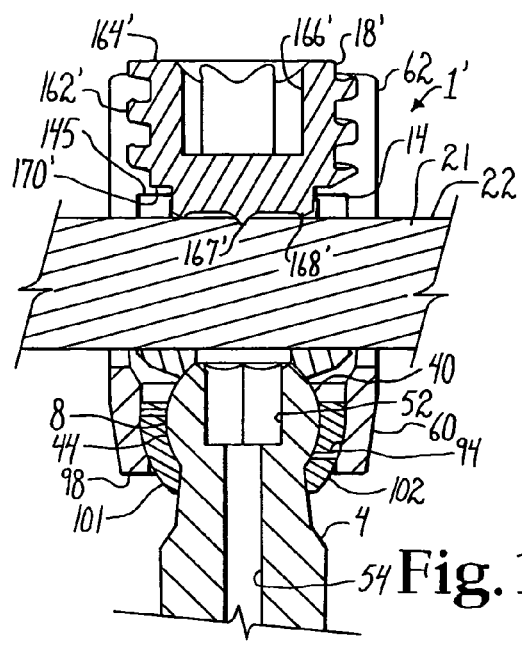
FIG. 14 is an enlarged and partial cross-sectional view taken along the line 14-14 of FIG. 13.
Figure 15:
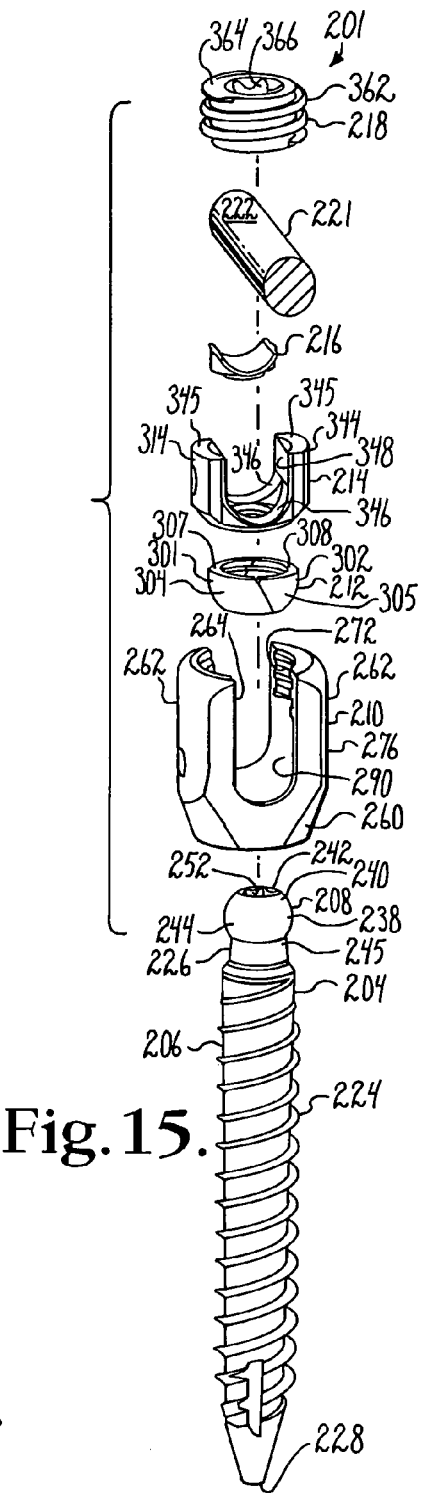
FIG. 15 is an enlarged and partial exploded perspective view of a second, alternative embodiment of a polyaxial bone screw assembly according to the present invention including a shank, a receiver, a retainer having two discreet pieces, a compression insert, a pivot insert, and a closure top, and further shown with a longitudinal connecting member in the form of a rod.

With reference to FIGS. 12, 13 and 14, the illustrated elongate rod or longitudinal connecting member 21 can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials.

Longitudinal connecting members for use with the assembly 1 may take a variety of shapes, including but not limited to rods or bars of oval, rectangular or other curved or polygonal cross-section. The shape of the insert 14 channel or saddle 146 may be modified so as to closely hold, and if desired, fix the longitudinal connecting member to the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a u-shaped channel (or rectangular- or other-shaped channel) for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1, 8 and 9, the first closure structure or closure top 18 shown with the assembly 1 is rotatably received between the spaced arms 62. It is noted that the closure 18 can be any of a variety of different types of closure structures for use in conjunction with the present invention with suitable mating structure on the upstanding arms 62. It is also foreseen that the closure top could be a twist-in or slide-in closure structure. The illustrated closure structure 18 is substantially cylindrical and includes an outer helically wound guide and advancement structure 162 in the form of a flange form that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 62 and having such a nature as to resist splaying of the arms 62 when the closure structure 18 is advanced into the U-shaped channel 64. The illustrated closure structure 18 also includes a top surface 164 with an internal drive 166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 166 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 168 of the closure is illustrated as planar, but may include a point, points, a rim or roughening for engagement with the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

With particular reference to FIGS. 8 and 9, the closure top 18 is shown fully assembled with the receiver 10 and the insert 14, but without the rod 21 or any other longitudinal connecting member. The closure top 18 includes an annular base rim or step 170 adjacent the bottom surface 168. The closure structure 18 is sized and shaped such that the annular rim 170 engages the top surfaces 145 of the insert 14 and presses the insert 14 down into pressing engagement with the shank upper portion 8 to lock the shank 4 in place with respect to the receiver 10. Thus, in some embodiments of the invention, the assembly 1 cooperates with a rod, cord, cable or other longitudinal connecting member to capture such connecting member within the receiver 10, but to allow the connector some freedom of movement within the receiver 10. In such applications, elastic spacers can be positioned around the connecting member and between the receivers. The closure 18 and insert 14 combination may also be desirable when the connecting member is made from a deformable plastic. In such embodiments, the closure bottom surface 168 may engage and frictionally hold the connecting member in place, but the polyaxial mechanism is firmly locked in place by the closure 18 directly engaging and pressing upon the insert 14 that in turn presses on the shank upper portion, desirably holding, but not over-stressing the longitudinal connecting member at the cite of engagement with the bone screw. Also, if a longitudinal connecting member would eventually become partially or totally disengaged from the closure bottom surface 168, for example, if a plastic connecting member exhibits creep, the shank 4 would advantageously remain fixed in position with respect to the receiver regardless of any movement of the connecting member within the receiver.

With reference to FIGS. 10-14 the assembly 1 of FIG. 1 is shown with the rod 22 and a modified closure top 18'. Thus, the assembly shown in FIGS. 12-14 is identified herein as the assembly 1'. The top 18' includes a guide and advancement structure 162', a top 164' and an internal drive 166' identical or substantially similar in form and function to the respective guide and advancement structure 162, top 164, and internal drive 166 of the closure top 18 previously described herein. Furthermore, the closure top 18' includes a point 167' and rim 168' bottom or base feature as compared to the planar bottom 168 of the closure top 18. Similar to the closure top 18, the top 18' includes an annular step or rim 170' that in some embodiments may frictionally engage the insert 14 similar to the step or rim 170 of the closure top 18. However, in the embodiment shown in FIGS. 12-14, the point 167' and the rim 168' frictionally engage the rod 21, while the step 170' remains spaced from top surfaces 145 of the insert 14. The pressure of the closure top 18' bearing down on the rod 21 in turn presses the rod against the insert 14 thereby pressing the insert 14 into engagement with the bone screw shank upper portion 8. Specifically, the rod 21 is cradled by and directly or abuttingly engages the insert 14 at the saddle 146, as shown in FIGS. 13 and 14 and 14 is biased against the saddle 146 by pressure from the closure structure 18', consequently biasing the insert surface 142 against the shank upper portion 8 spherical surface portion 40, pressing the shank 4 downwardly in a direction toward the base 60 of the receiver 10 when the assembly 1 is fully assembled, ultimately pressing the retainer pieces 101 and 102 into frictional engagement with the receiver seating surface 94, thereby locking the polyaxial mechanism of the bone screw assembly 1'. The shank 4 and retainer structure pieces 12 are thereby locked or held in position relative to the receiver 10 by the rod 21 firmly pushing downward on the insert 14 that in turn pushes down on the shank upper surface 40.

Figure 6:
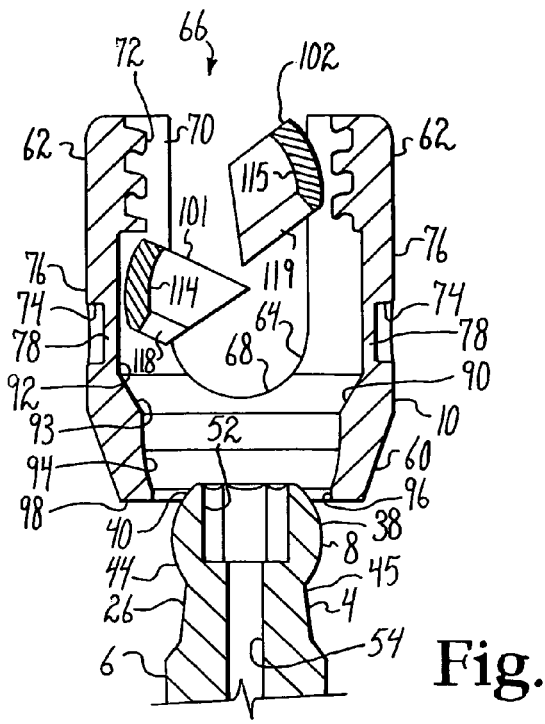
FIG. 6 is an enlarged and partial front elevational view of the shank, retainer pieces and receiver of FIG. 1 with portions broken away to show the detail thereof and shown in an early stage of assembly.

Prior to the polyaxial bone screw assembly 1 or 1' being placed in use according to the invention, the retainer structure pieces 101 and 102 are typically first inserted or top-loaded into the receiver U-shaped channel 64 at the opening 66, as shown in FIG. 6, and then into the cavity 90 to ultimately dispose the structure pieces 12 adjacent to the inner surface 94 of the receiver 10. Alternatively, one of the retainer structure pieces 101 may be inserted or top-loaded into the channel 64 at the opening 66, while the other retainer structure piece 102, may inserted or bottom-loaded into the cavity 90 at the lower neck 96. Alternatively, both pieces 101 and 102 may be uploaded at the neck 96.

Figure 7:
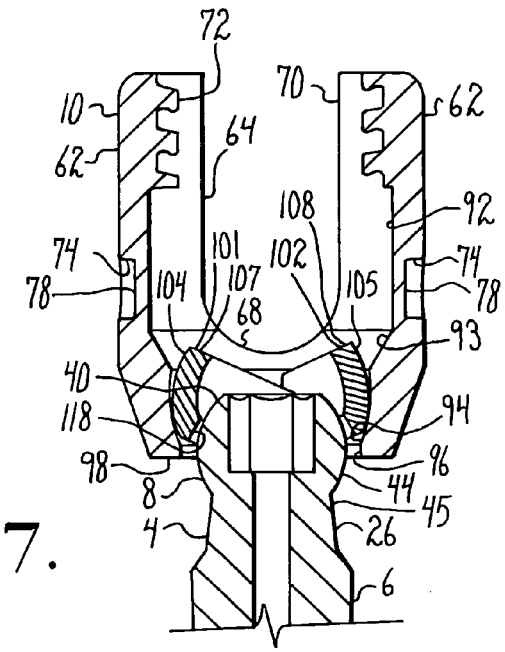
FIG. 7 is an enlarged and partial front elevational view with portions broken away, similar to FIG. 6, shown in a later stage of assembly.

With reference to FIG. 7, after the retainer pieces 101 and 102 are disposed in the cavity 90, the shank 4 is inserted or up-loaded into the receiver 10 at the neck 96. The spherical body 38 of the shank upper portion 8 comes into contact with the inner surfaces 114 and 115 of the respective retainer pieces 101 and 102. Initially all three components, the shank upper portion 8, and the pieces 101 and 102 may move upwardly into the cavity 90. As the shank upper portion 8 continues to move upwardly and into the cavity 90, the retainer structure pieces 101 and 102 pivot about edges thereof and then begin to move downwardly toward the base 60 until in operational alignment as shown, for example, in FIGS. 8, 9, 13 and 14, with the inner frusto-conical surfaces 118 and 119 abutting and seated upon the surface 45 of the shank neck 26. At the same time, the inner spherical surfaces 114 and 116 frictionally engage the lower spherical surface portion 44 of the shank upper portion 8. Subsequent slight downward movement (directed away from the top opening 66) by the shank 4, as well as the frictionally engaged retainer pieces 101 and 102, seats the shank/retainer structure assembly in the receiver cavity 90, with the retainer outer spherical surfaces 104 and 105 in sliding engagement with the receiver seating surface 94. The retainer structure pieces 12, now fully seated in the receiver 10 are coaxially aligned with the shank upper portion. At this time, the shank upper portion 8, the retainer structure 12, the receiver seating surface 94 and the lower aperture or neck 96 cooperate to maintain the shank body 6 in pivotal and rotational relation with the receiver 10. Only the retainer structure 12 is in slidable engagement with the receiver spherical seating surface 94. Both the shank upper portion 8 and the threaded portion of the shank body 6 are in spaced relation with the receiver 10. At this point there is no substantial outward or downward pressure on the shank upper portion 8 so the retainer 12 easily rotates with the shank 6 within the receiver chamber, such rotation being of a ball and socket type with the angle of rotation restricted only by engagement of the shank neck 26 with the neck 96 of the receiver 10. A spring-ring located between the upper portion 8 and retainer 12 can provide frictional engagement between the parts to stabilize and minimize unwanted movement with respect to the shank during rod insertion.

Then, the insert 14 is inserted into the receiver channel 64 at the opening 66 with the arms 144 aligned in the channel 64 between the guide and advancement structures 72. The insert 14 is then moved downwardly in the channel and toward the cavity 90. Once the arms 144 are located generally below the guide and advancement structure 72, the insert 14 is rotated about the axis B of the receiver 10. The arms 144 fit within the cylindrical walls 92. Once the arms 144 are located directly below the guide and advancement structures 72, rotation is ceased and a tool (not shown) is used to press the thin walls 78 of the receiver 10 into the recesses 156 of the insert 14. The insert 14 is now locked into place inside the receiver 10 with the guide and advancement structures 72 prohibiting upward movement of the insert 14 out of the channel 64. As illustrated in FIGS. 8, 9, 14 and 15, the insert 14 seats on the shank upper portion surface 40 with the surface 142 in sliding engagement with the surface 40. A run-out or relief area of the surface 92 located directly beneath the receiver guide and advancement structure 72 is sized and shaped to allow for some upward and downward movement of the insert 14 toward and away from the shank upper portion 8 such that the shank 4 is freely pivotable with respect to the receiver 10 until the insert 14 is pressed down upon the upper portion 8, placing the shank upper portion 8 into locking frictional engagement with the receiver 10 at the surface 94. With respect to the assembly 1, the shank is locked into place by pressure from the closure structure 18 onto the insert 14, while in the assembly 1', the closure structure 18' presses on the rod 21 that in turn presses on the insert 14 that in turn presses down upon the shank upper portion 8.

The bone screw assembly made up of the assembled shank 4, receiver 10, retainer pieces 12 and insert 14 is then normally screwed into a bone, such as vertebra, by rotation of the shank 4 using a suitable driving tool (not shown) that operably drives and rotates the shank body 6 by engagement thereof at the internal drive 52. Specifically, the vertebra (not shown) may be pre-drilled to minimize stressing the bone and have a guide wire (not shown) inserted to provide a guide for the placement and angle of the shank 4 with respect to the vertebra. A further tap hole may be made using a tap with the guide wire as a guide. Then, the bone screw assembly is threaded onto the guide wire utilizing the cannulation bore 54 by first threading the wire into the opening at the bottom 28 and then out of the top opening at the drive feature 52. The shank 4 is then driven into the vertebra using the wire as a placement guide. It is foreseen that the bone screw assemblies 1, 1', the rod 21 (also having a central lumen in some embodiments) and the closure top 18 or 18' (also with a central bore) can be inserted in a percutaneous or minimally invasive surgical manner, utilizing guide wires.

With reference to FIGS. 13 and 14, for example, of the assembly 1', the rod 21 is eventually positioned in an open or percutaneous manner in cooperation with the at least two bone screw assemblies 1'. Alignment of the rod surface 22 with the saddle 146 of the insert 14 is initially provided and then maintained by the crimped walls 78 of the receiver 10. The closure structure 18' is then inserted into and advanced between the arms 62 of each of the receivers 10. The closure structure 18' is rotated, using a tool engaged with the inner drive 166' until a selected pressure is reached at which point the rod 21 engages the saddle 146 and the rod is urged toward, but not in contact with the lower seat of the receiver 10 that defines the U-shaped channel 64. For example, about 80 to about 120 inch pounds pressure may be required for fixing the bone screw shank 6 with respect to the receiver 10.

As the closure structure 18' rotates and moves downwardly into the respective receiver 10, the point 167' and rim 168' engage and penetrate the rod surface 22, the closure structure 18' pressing against and biasing the rod 21 into engagement with the compression insert 14 that operably produces a frictional engagement between the insert surface 142 and the shank surface 40 and also urges the shank upper portion 8 toward the retainer 12 and, in turn, the structure 12 in a direction toward the base 60 of the receiver 10, so as to frictionally seat the spherical surfaces 104 and 105 against the internal spherical seating surface 94 of the receiver 10, also fixing the shank 4 and the retainer 12 in a selected, rigid position relative to the receiver 10. At this time it is also possible for the retainer 12 to expand somewhat for an even tighter fit in the receiver cavity lower seat 94.

If removal of the rod 21 from any of the bone screw assemblies 1 or 1' is necessary, or if it is desired to release the rod 21 at a particular location, disassembly is accomplished by using the driving tool (not shown) that mates with the internal drive 166 or 166' on the closure structure 18 or 18' to rotate and remove such closure structure from the cooperating receiver 10. Disassembly is then accomplished in reverse order to the procedure described previously herein for assembly.

With reference to FIGS. 15-25, a second embodiment of a polyaxial bone screw according to the invention, generally 201, includes a shank 204 having a body 206 and an upper portion 208, a receiver 210, a two-piece retainer 212, a compression insert 214, a pivot insert 216 and a closure structure 218 and is shown with a longitudinal connecting member in the form of a hard, inelastic, substantially non-deformable rod 221 having a substantially cylindrical outer surface 222. It is noted that the illustrated inserts and cooperating features of bone screws according to the invention may also be used with one-piece retainers or rings.

The shank 204 is identical or substantially similar in form and function to the shank 4 previously described herein with respect to the assembly 1. Thus, the shank 204 includes a thread 224, a neck 226, a tip 228, a spherical body 238 with an upper surface portion 240, a planar annular top 242, a lower surface portion/seating surface 244, a shank neck portion 245, and an internal drive 252 that are the same or similar in form and function to the respective thread 24, neck 26, tip 28, spherical body 38 with upper surface portion 40, planar annular top 42, lower surface portion/seating surface 244, shank neck portion 245, and internal drive 252 of the shank 4 of the assembly 1.

The receiver 210 is identical or substantially similar in form and function to the receiver 10 previously described herein with respect to the assembly 1. Thus, the receiver 210 includes a receiver base 260, a pair of upstanding arms 262, a U-shaped channel 264, guide and advancement structures 272, apertures 274, outer arm surfaces 276, inner walls 278, a cavity or chamber 290, upper inner cylindrical walls 292, spherical seating surface 294, a neck 296 and a lower exterior 298 that are the same or similar in form and function to the respective receiver base 60, pair of upstanding arms 62, U-shaped channel 64, guide and advancement structures 72, apertures 74, outer arm surfaces 76, inner walls 78, cavity or camber 90, upper inner cylindrical walls 92, spherical seating surface 94, neck 96 and a lower exterior 98 of the receiver 10 of the assembly 1.

The two piece retainer 212 is identical or substantially similar in form and function to the two-piece retainer 12 previously described herein with respect to the assembly 1. Thus, the retainer 212 includes a first piece 301 and a second piece 302 having respective outer spherical surfaces 304 and 305, respective top surfaces 307 and 308, respective inner spherical surfaces 314 and 315, respective inner frusto-conical surfaces 318 and 319 that are the same or similar in form and function as the respective first piece 101, second piece 102, respective outer spherical surfaces 104 and 105, respective top surfaces 107 and 108, respective inner spherical surfaces 114 and 115 and respective frusto-conical surfaces 118 and 119 of the retainer 12 of the assembly 1, as well as all other features thereof.

The compression insert 214 is substantially similar in form and function to the insert 14 previously described herein with respect to the assembly 1. Thus, the insert 214 includes a cylindrical inner surface 341, an inner spherical surface 342, a pair of spaced opposed arms 344 having top surfaces 345, a pair of saddle shaped surfaces 346, a lower planar surface 347, inner planar arm surfaces 348, a saddle lower seat 350, a bottom surface 352, a base outer surface 354, outer arm surfaces 355, each having a groove or depression 356 that are the same or similar in form and function to the respective cylindrical inner surface 141, inner spherical surface 142, pair of spaced opposed arms 144 having top surfaces 145, pair of saddle shaped surfaces 146, lower planar surface 147, inner planar arm surfaces 148, saddle lower seat 150, bottom surface 152, base outer surface 154, and outer arm surfaces 155, each having a groove or depression 156 previously described herein with respect to the assembly 1. Unlike the assembly 1, the compression insert 214 of the assembly 201 further engages the pivot insert 216 at the planar surface 345, with the cylindrical surface 341 receiving a portion of the pivot insert 216 as will be discussed in greater detail below.

The closure top 218 is substantially similar in form and function to the top 18 previously described herein with respect to the assembly 1 with the exception of a bottom surface thereof. Thus, the closure top 218 includes a guide and advancement structure 362, a top surface 364, an internal drive 366 and a bottom rim 370 that is identical or substantially similar in form and function to the respective guide and advancement structure 162, the top surface 164, the internal drive 166 and the bottom annular planar rim surface 170 of the closure top 18 previously described herein with respect to the assembly 1. As shown, for example, in FIGS. 22 and 23, the closure top 218 is sized and shaped so that the bottom rim 370 directly frictionally engages the top surface 345 of the compression insert 214, pushing the insert 214 in a direction toward the receiver base 260 so that the insert 214 directly frictionally engages the shank upper portion 208 at the spherical surface 240 pushing the shank 204 downwardly and thus pressing the retainer pieces 212 into frictional engagement with the receiver spherical seat 294. Therefore, locking of the polyaxial mechanism is not solely dependent upon the closure top 218 pressing on the rod 221 that in turn presses the compression insert 214 into engagement with the shank 204.

Also, the closure top 218, rather than having a planar bottom surface such as the bottom surface 168 of the closure top 18, has a substantially domed or spherical bottom surface 368. As will be described in greater detail below, the spherical surface 368 of the closure top 218 cooperates with a curved surface of the pivot insert 216 allowing for operative angulation or pivoting movement of the longitudinal connecting member disposed therebetween in the sagittal plane.

With particular reference to FIGS. 16-21, the illustrated pivot insert 216 is sized and shaped to be received by and downloaded into the receiver 10 at the upper opening 66, followed by insertion into the previously inserted compression insert 214. The pivot insert 216 has an operational central axis that is the same as the central axis of the receiver 210 and the compression insert 214. A concave, substantially spherical bottom surface 379 of the insert 216 has a radius that is substantially the same or only slightly larger than the radius of the spherical body 238 of the upper portion 208 of the shank 204, the surface 379 being sized and shaped to slidingly receive the upper surface portion 240 of the spherical body 238 when the pivot insert is seated within the compression insert 214. The concave surface 379 partially defines an otherwise substantially cylindrical base 380 of the pivot insert 216, the base 380 having a substantially planar annular bottom rim surface 381 disposed about the spherical surface 379. The base 380 is sized and shaped to be received within the inner cylindrical surface 341 of the compression insert 214. The base 380 is integral with a substantially ellipsoid body 382 that has a planar substantially oval-shaped bottom surface 383 that extends outwardly from either side of the base 380 and forms a pair of upwardly extending arms 384 that support an integral substantially U- or saddle-shaped portion 385 that extends between the arms 384 and over the base 380. Each of the arms 384 and the saddle 385 terminate at substantially planar, parallel upper surfaces or strips 386. The arms 384 are sized and shaped to fit between the saddle surfaces 346 of the compression insert 214 with the bottom surface 383 being seated on the surface 347 of the compression insert 214. The saddle further includes an under surface 387 and opposed, parallel substantially planar outwardly facing side surfaces 388 that run substantially perpendicular to the upper surfaces 386. As best shown in FIG. 19, a longitudinal connecting member seating surface 389 of the saddle 385 further includes an elevation or rounded ridge 390 that curves upwardly from each of the side surfaces 388 and is at a highest elevation thereof substantially centrally located between the side surfaces 390, allowing for some angular motion of the connecting member or rod 221 in the sagittal plane when the assembly 201 is fully assembled with the rod 221 and implanted in a patient's spine along with at least one other bone anchor. Thus, with particular reference to FIG. 25, in operation, both the convex surface 390 of the insert 216 and the convex surface 368 of the closure top 218 engage the rod 121 at the surface 222, with a degree of angulation of the rod 221 shown in phantom and identified as 221'.

In use, the shank 204, the retainer pieces 212 and the compression insert 214 of the assembly 201 are assembled in a manner identical or substantially similar to the manner of assembly previously described herein with respect to the shank 4, retainer pieces 12 and compression insert 14 of the assembly 1. The assembled shank 204, retainer 212 and compression insert 214 are then implanted on a human spine in a manner identical or substantially similar to the manner previously described herein with respect to the assembly 1. The screw driver is removed and the receiver can be angulated with respect to the shank. Prior to insertion of the rod 221 into cooperating bone screw receivers 210, an optional pivot insert 216 can be inserted into the U-shaped channel 264 of each of the receivers 210 and then into each compression insert 214 with the arms 384 of the pivot insert 216 aligned with the arms 344 of the pressure insert 214, the arms 384 being received between the pair of saddle surfaces 346 until the planar surface 383 of the pivot insert 216 seats on the planar surface 347 of the compression insert 214 and the cylindrical base 380 of the pivot insert 216 is received within the inner cylindrical surface 341 of the compression insert 214.

With particular reference to FIGS. 24 and 25, the rod 221 is eventually positioned in an open or percutaneous manner in cooperation with the at least two bone screw assemblies 201. Optional (elastic) sleeves on the rod can be used between the assemblies 201. Alignment of the rod surface 222 with the saddle surfaces 346 of the insert 214 is initially provided and then maintained by the previously crimped walls 278 of the receiver 210. The closure structure 218 is then inserted into and advanced between the arms 262 of each of the receivers 210. The closure structure 218 is rotated, using a tool engaged with the inner drive 366 until a selected pressure is reached at which point the rod 221 is captured between the saddle surfaces 346 of the compression insert 214, and in some embodiments, frictionally engages both the curved surface 390 of the pivot insert seating portion 389 and the convex surface 368 of the closure top 218. In other embodiments, the rod 221 can be captured, but not locked in place. Also, as the closure structure 218 rotates and moves downwardly into the respective receiver 210, the rim 370 frictionally engages the top surfaces 345 of the arms of the compression insert 214. Thus, in this embodiment, the closure top 218 presses against and biases the rod 21 into engagement with the pivot insert 216 that in turn presses against the compression insert 214 and the closure top 218 also presses directly against the insert 214 to securely lock the polyaxial mechanism of the assembly 201 by fixing the shank 204 and the retainer 212 in a selected, rigid position relative to the receiver 210. At this time it is also possible for the retainer 212 to expand somewhat for an even tighter fit in the receiver cavity lower seat 294.

If removal of the rod 221 from any of the bone screw assemblies 201 is necessary, or if it is desired to release the rod 221 at a particular location, disassembly is accomplished by using the driving tool (not shown) that mates with the internal drive 366 on the closure structure 218 to rotate and remove such closure structure from the cooperating receiver 210. Disassembly is then accomplished in reverse order to the procedure described previously herein for assembly.

Figure 26:
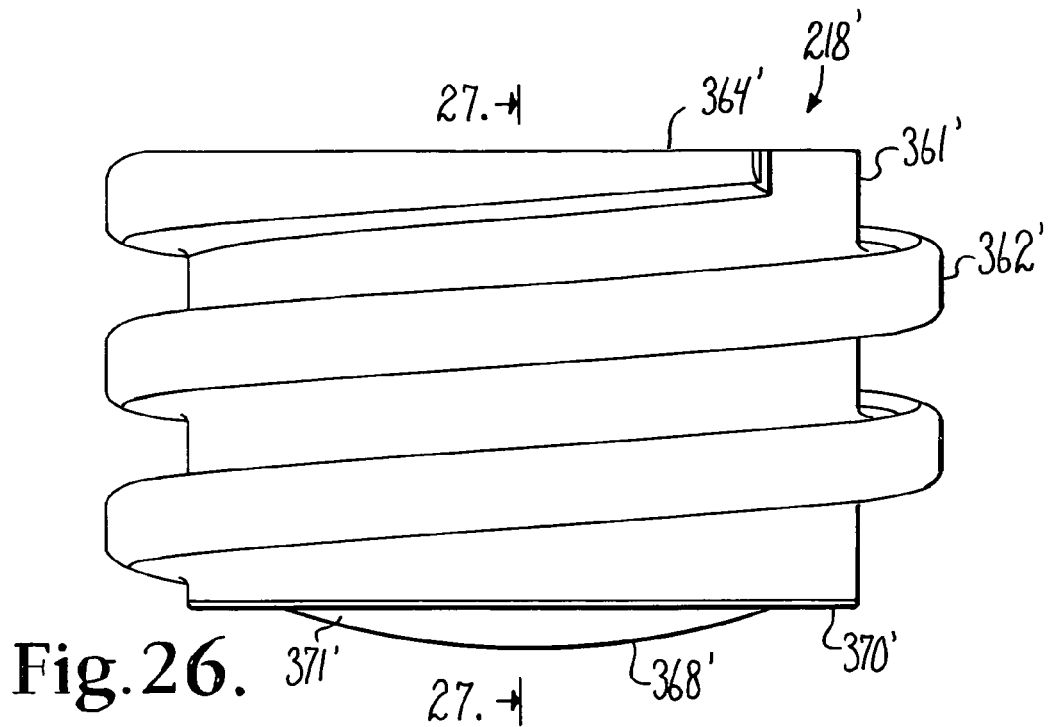
FIG. 26 is an enlarged front elevational view of an alternative closure top for use with assemblies of the invention.
Figure 27:
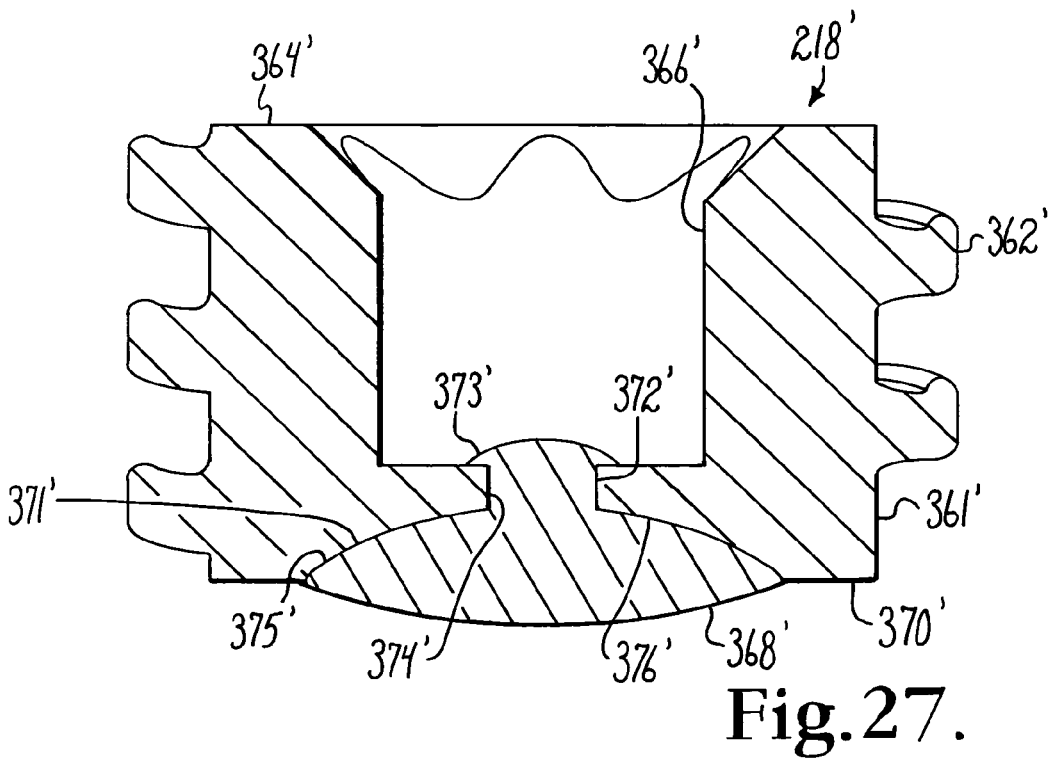
FIG. 27 is an enlarged cross-sectional view taken along the line 27-27 of FIG. 26.

It is noted that the bone screw components of the assemblies 1, 1' and 201 according to the invention previously described herein are typically made from a variety of materials, most typically metal and metal alloys including but not limited to stainless steel, titanium, and titanium alloys. A desirable material that provides for low wear debris, a desirable coefficient of friction and good fatigue resistance for the rod 221, for example, is cobalt chrome. Particularly if the rod 221 used with the assembly 201 is made from cobalt chrome, it is desirable for the pivot insert 216 and the closure surface 368 that engage the rod 221 to also be made from cobalt chrome. However, cobalt chrome is not necessarily well suited for closure top and receiver components of the invention due to its hardness. With reference to FIGS. 26 and 27, a two-part or piece closure 218' is illustrated wherein a domed bottom surface portion 368' is separate from a remainder of the closure 218'. Thus, the domed bottom surface 368' may advantageously be made from a first material, such as cobalt chrome, and a remainder of the closure 218' may advantageously be made from a second material, such as stainless steel or titanium.

The alternative closure top 218' shown in FIGS. 26 and 27 may be an alternative or substitute for the top 218 of the assembly 201 of the invention. The top 218' includes a body portion 361' having a guide and advancement structure 362', a top surface 364', an internal drive 366', and a bottom rim 370' substantially similar to the guide and advancement structure 362, top surface 364, internal drive 366 and bottom rim 370 of the closure top 218 previously described herein with respect to the assembly 201. The closure top 218' further includes a separate or distinct bottom cap 371' having the domed bottom surface portion 368'. The bottom cap 371' further includes a neck 372' with an end surface portion 373' that is pressed upwardly into a small through bore 374' of the body portion 361' that communicates with the internal drive 366' until the end surface 373' is fully within a space formed by such drive 366'. Thereafter, the end surface 373' or neighboring surfaces of the body portion 361' that form the bore 374' may be worked so as to securely capture the neck end portion 373' within the drive, for example, shown as an enlarged or lipped domed end surface 373' in FIG. 27. As illustrated, the bottom cap 371' further includes an upper convex spherical surface 375' that is closely received by a lower concave spherical surface 376' of the body portion 361', the surface 376' being disposed within and above the rim 370'. Thus, the lipped or otherwise enlarged end portion 373' of the neck 372' is held within the internal drive 366' of the body portion 361' by such lip and cannot slip through the smaller through bore 374', with the spherical surface 375' being held fully and securely against the spherical surface 376'. When the rod 221 is made from cobalt chrome, the pivot insert 216 and the bottom cap 371' of the closure top 218' may also be made from cobalt chrome, advantageously providing cobalt chrome to cobalt chrome low frictional interfaces with the resultant good fatigue characteristics and desirable good wear, low debris attributes, while at the same time retaining the favorable features of mating titanium guide and advancement structures between the closure top 218' and the receiver 210.

With reference to FIGS. 28-47, a third embodiment of a polyaxial bone screw according to the invention, generally 401, includes a shank 404 having a body 406 and an upper portion 408, a receiver 410, a two-piece retainer 412, a compression insert 414, a pivot insert 416 and a closure structure or top 418 and is shown with a longitudinal connecting member in the form of a rod 421 having a substantially cylindrical outer surface 422. The shank 404, retainer 412, compression insert 414, pivot insert 416, closure top 418 and rod 421 are substantially similar in form, function and materials to the respective shank 204, retainer 212, compression insert 214, pivot insert 216, closure top 218 and rod 221 previously described herein with respect to the assembly 201. However, some of the above-listed components of the assembly 401 include a few additional and/or alternative features. Therefore, each of the assembly components shall be briefly described below.

With particular reference to FIGS. 28 and 43-47, the shank 404 is identical or substantially similar in form and function to the shank 204 previously described herein with respect to the assembly 201. Thus, the shank 404 includes a thread 424, a neck 426, a tip 428, a spherical body 438 with an upper surface portion 440, a planar annular top 442, a lower surface portion/seating surface 444, a shank neck portion 445, and an internal drive 452 that are the same or substantially similar in form and function to the respective thread 224, neck 226, tip 228, spherical body 238 with upper surface portion 240, planar annular top 242, lower surface portion/seating surface 244, shank neck portion 245, and internal drive 252 of the shank 204 of the assembly 201.

With particular reference to FIGS. 28, 30-32 and 43-47, the receiver 410 is substantially similar in form and function to the receiver 210 previously described herein with respect to the assembly 201 with the exception of a feature for placement and holding of the compression insert 414 in a desired aligned orientation. Thus, the receiver 410 includes a receiver base 460, a pair of upstanding arms 462, a U-shaped channel 464, guide and advancement structures 472, apertures 474, outer arm surfaces 476, inner thin walls 478, a cavity or chamber 490, upper inner cylindrical walls 492, spherical seating surface 494, a neck 496 and a lower exterior 498 that are the same or similar in form and function to the respective receiver base 260, pair of upstanding arms 262, U-shaped channel 264, guide and advancement structures 272, apertures 274, outer arm surfaces 276, inner walls 278, cavity or camber 290, upper inner cylindrical walls 292, spherical seating surface 294, neck 296 and lower exterior 298 of the receiver 210 of the assembly 201.

Figure 31:
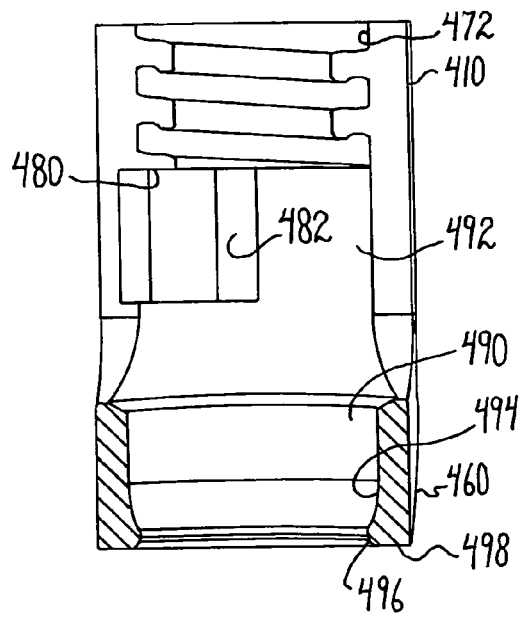
FIG. 31 is an enlarged side elevational view of the receiver of FIG. 28 with portions broken away to show the detail thereof.
Figure 32:
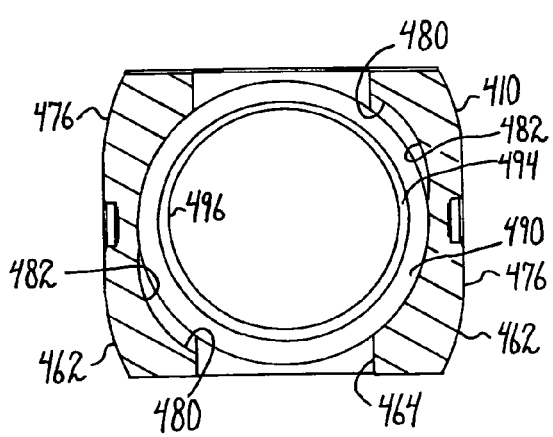
FIG. 32 is an enlarged cross-sectional view taken along the line 32-32 of FIG. 30.
Figure 33:
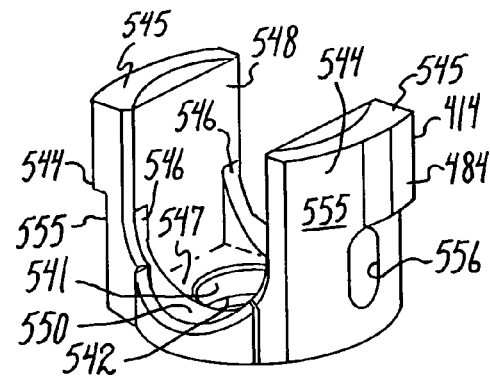
FIG. 33 is an enlarged perspective view of the compression insert of FIG. 28.
Figure 34:
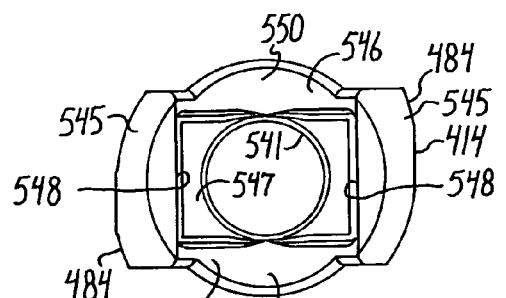
FIG. 34 is an enlarged top plan view of the compression insert of FIG. 28.
Figure 35:
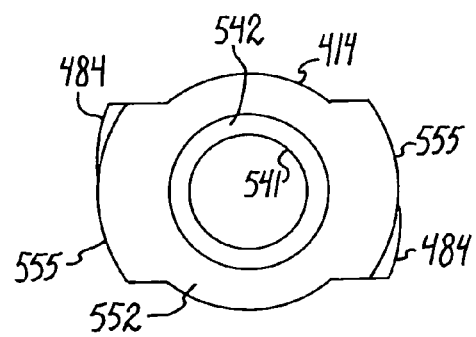
FIG. 35 is an enlarged bottom plan view of the compression insert of FIG. 28.
Figure 36:
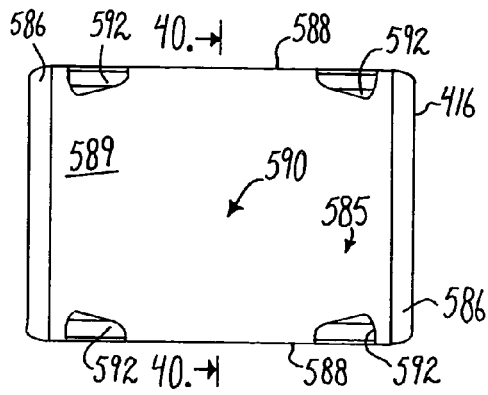
FIG. 36 is an enlarged top plan view of the pivot insert of FIG. 28.
Figure 38:
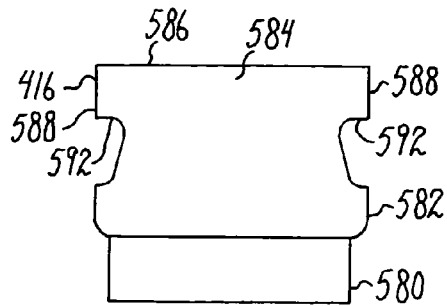
FIG. 38 is an enlarged side elevational view of the pivot insert of FIG. 36.
Figure 37:
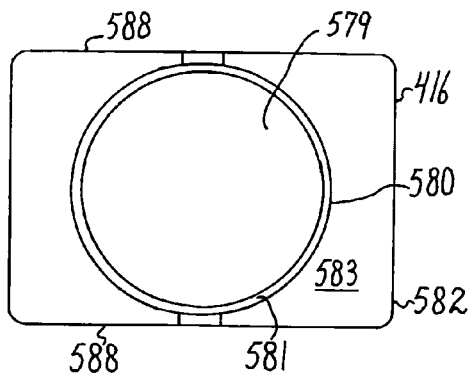
FIG. 37 is an enlarged bottom plan view of the pivot insert of FIG. 36.
Figure 39:
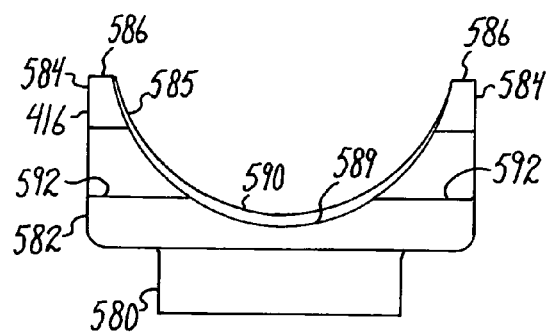
FIG. 39 is an enlarged front elevational view of the pivot insert of FIG. 36.
Figure 40:
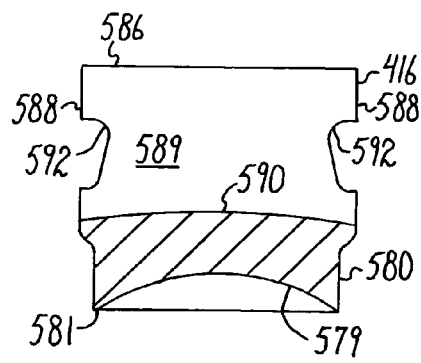
FIG. 40 is an enlarged cross-sectional view taken along the line 40-40 of FIG. 36.
Figure 41:
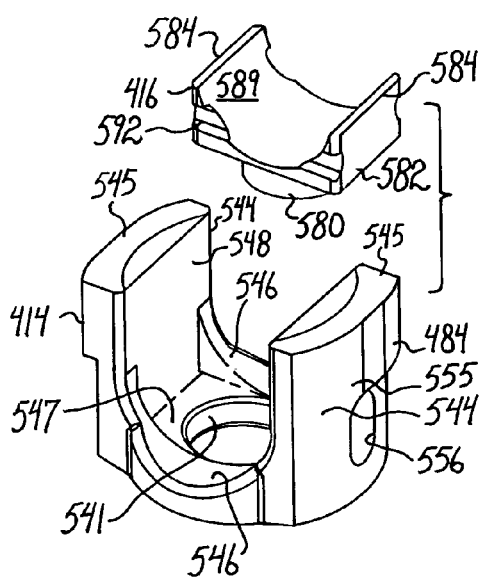
FIG. 41 is an enlarged perspective view of the pivot insert and compression insert of FIG. 28.
Figure 42:
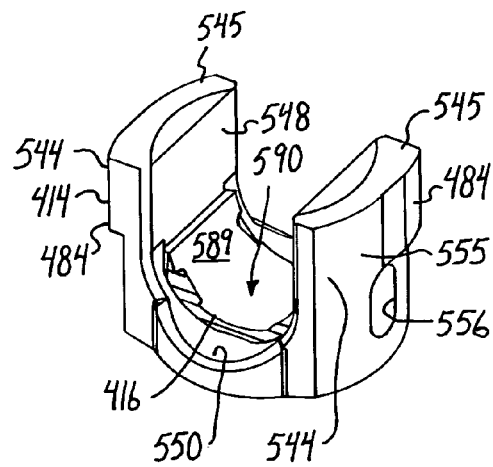
FIG. 42 is an enlarged perspective view of the pivot insert and compression insert of FIG. 41 shown assembled.

Furthermore, with particular reference to FIGS. 30-32, formed within each of the substantially cylindrical surfaces 492 and located directly beneath the guide and advancement structure 472 of both the arms 462 is a recess 480 partially defined by a rounded stop or abutment wall 482. As will be described in greater detail below, the cooperating compression insert 414 includes a cooperating structure 484 that extends outwardly from each arm thereof that abuts against the respective abutment wall 482 of each of the receiver arms, providing a centering stop or block when the insert 414 is rotated into place in a clockwise manner as will be described below.

With particular reference to FIGS. 28, 29 and 43-47, the two piece retainer 412 is substantially similar in form and function to the two-piece retainer 212 previously described herein with respect to the assembly 201. Thus, the retainer 412 includes a first piece 501 and a second piece 502 having respective outer spherical surfaces 504 and 505, respective top surfaces 507 and 508, respective inner spherical surfaces 514 and 515, respective inner frusto-conical surfaces 518 and 519 that are the same or similar in form and function as the respective first piece 301, second piece 302, respective outer spherical surfaces 304 and 305, respective top surfaces 307 and 308, respective inner spherical surfaces 314 and 315 and respective frusto-conical surfaces 318 and 319 of the retainer 212 of the assembly 201, as well as all other features thereof. Furthermore, formed in each of the top surfaces 507 and 508 are respective curved notches 522 and 523. The notch 522 is located near an end wall 532 of the piece 501 and the notch 523 is located near an end wall 534 of the piece 502. In operation, the notches 522 and 523 are disposed opposite one another. The notches 522 and 523 are each substantially U- or C-shaped and extend between inner and outer spherical surfaces of the respective pieces 501 and 502. The notches 522 and 523 provide clearance during assembly and, if needed, disassembly of the pieces 501 and 502 about the shank upper portion 408 within the receiver 410.

With particular reference to FIGS. 33-35 and 41-44, the compression insert 414 is substantially similar in form and function to the insert 214 previously described herein with respect to the assembly 201. Thus, the insert 414 includes a cylindrical inner surface 541, an inner spherical surface 542, a pair of spaced opposed arms 544 having top surfaces 545, a pair of saddle shaped surfaces 546, a lower planar surface 547, inner planar arm surfaces 548, a saddle lower seat 550, a frusto-conical bottom surface 552, outer arm surfaces 555, each having a groove or depression 556 that are substantially similar in form and function to the respective cylindrical inner surface 341, inner spherical surface 342, pair of spaced opposed arms 344 having top surfaces 345, pair of saddle shaped surfaces 346, lower planar surface 347, inner planar arm surfaces 348, saddle lower seat 350, bottom surface 352 and outer arm surfaces 355, each having a groove or depression 356 previously described herein with respect to the assembly 201. Like the assembly 201, the compression insert 414 of the assembly 401 engages the pivot insert 416 at the planar surface 545, with the cylindrical surface 541 receiving a portion of the pivot insert 416 as will be discussed in greater detail below. Unlike the insert 214, the insert 414 planar seating surface 547 is slightly larger and substantially rectangular, providing greater surface contact with the pivot insert 416 and better access to tools if the pivot insert 416 needs to be removed, with the pivot insert 416 also including structure for manipulation thereof as will be described in greater detail below.

With particular reference to FIGS. 28 and 43-47, the closure top 418 is substantially similar in form and function to the top 218 previously described herein with respect to the assembly 201. Thus, the closure top 418 includes a guide and advancement structure 562, a top surface 564, an internal drive 566, a domed shaped bottom surface 568 and a bottom rim 570 that is identical or substantially similar in form and function to the respective guide and advancement structure 362, the top surface 364, the internal drive 366, domed bottom surface 368 and the bottom annular planar rim surface 370 of the closure top 218 previously described herein with respect to the assembly 201. As shown, for example, in FIG. 42, the closure top 418 is sized and shaped so that the bottom rim 570 directly frictionally engages the top surface 545 of the compression insert 414, pushing the insert 414 in a direction toward the receiver base 460 so that the insert 414 directly frictionally engages the shank upper portion 408 at the spherical surface 440 pushing the shank 404 downwardly and thus pressing the retainer pieces 412 into frictional engagement with the receiver spherical seat 494. Therefore, locking of the polyaxial mechanism is not dependent upon the closure top 418 pressing on the rod 421 that in turn places force on the compression insert 414 into engagement with the shank 404. The closure top 418 may also be replaced by the closure top 218' in some embodiments, particularly if the rod 421 is made from cobalt chrome and therefore the domed bottom surface 368' may also be made from cobalt chrome while the remainder of the closure top may be made from a different material.

With particular reference to FIGS. 28 and 36-47, the illustrated pivot insert 416 is substantially similar in form and function to the pivot insert 216 previously described herein with respect to the assembly 201. Thus, the pivot insert 416 includes a lower spherical surface 579, a cylindrical base 580, a bottom rim 581, a body 582, a body bottom surface 583, a pair of opposed arms 584, a saddle 585, planar arm top surfaces 586, opposed side surfaces 588, and a saddle seating surface 589 having an elevated portion or ridge 590 that is substantially similar in form and function to the respective lower spherical surface 379, cylindrical base 380, bottom rim 381, body 382, body bottom surface 383, pair of opposed arms 384, saddle 385, planar arm top surfaces 386, opposed side surfaces 388, and saddle seating surface 389 having an elevated portion or ridge 390 of the pivot insert 216. Unlike the pivot insert 216, the body 582 is of substantially rectangular cross-section as compared to the ovoid shape of the body 382 of the insert 216. The saddle 585 is also completely incorporated into the body 582 and fully integral and supported thereby. Furthermore, formed in the body 582 at each of the side surfaces 588 is a through-groove 592 that runs substantially parallel to the rectangular bottom surface 583 of the body 582. The through-grooves 592 are somewhat U-shaped and are carved more deeply into the side surfaces 588 in a direction of the top surfaces 586, providing a hook-like surface for a manipulation tool (not shown) to easily grasp the insert 416 during assembly, and if needed, during disassembly of the pivot insert 416 from the assembly 401.

Figure 44:
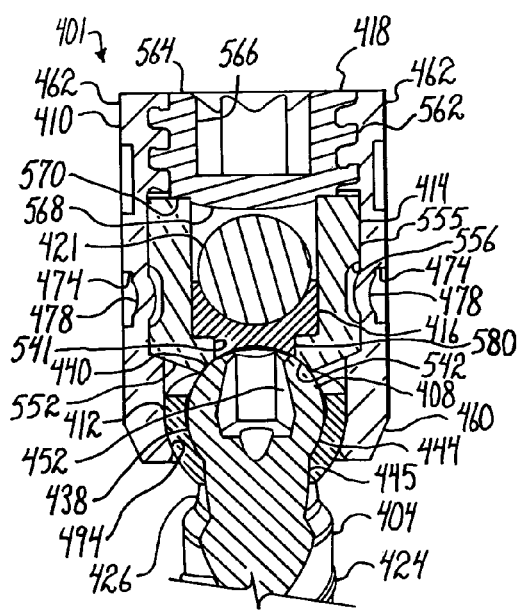
FIG. 44 is an enlarged and partial cross-sectional view taken along the line 44-44 of FIG. 43.
Figure 54:
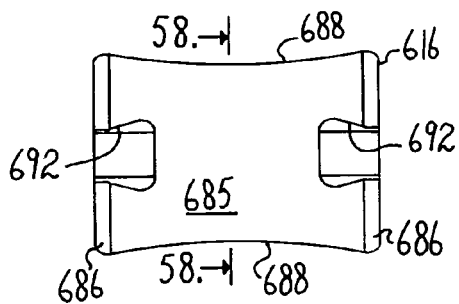
FIG. 54 is an enlarged top plan view of the connecting member support insert of FIG. 51.
Figure 56:
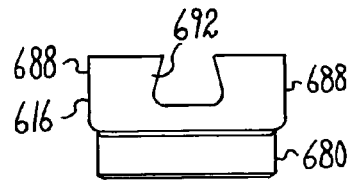
FIG. 56 is an enlarged side elevational view of the support insert of FIG. 54.
Figure 55:
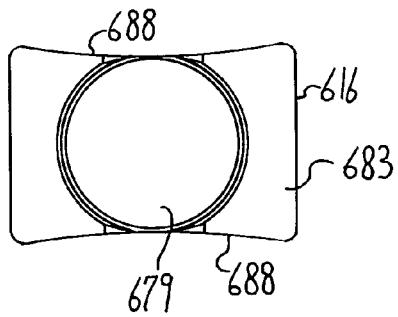
FIG. 55 is an enlarged bottom plan view of the support insert of FIG. 54.
Figure 57:
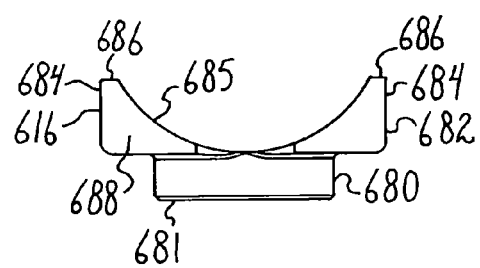
FIG. 57 is an enlarged front elevational view of the support insert of FIG. 54.
Figure 58:
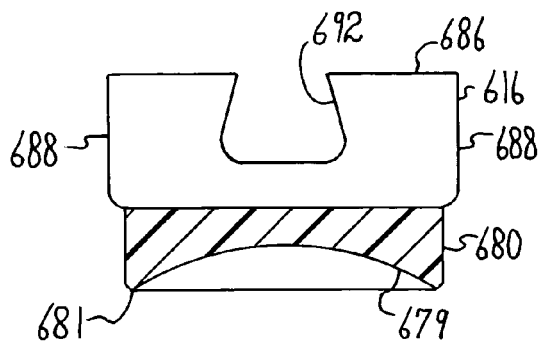
FIG. 58 is an enlarged cross-sectional view taken along the line 58-58 of FIG. 54.

In use, the shank 404, the retainer pieces 412 and the compression insert 414 of the assembly 401 are assembled in a manner identical or substantially similar to the manner of assembly previously described herein with respect to the shank 4, retainer pieces 12 and compression insert 14 of the assembly 1. Furthermore, the compression insert 414 protruding arms structures 484 are frictionally mated with the receiver wall surfaces 482 as follows: After top loading of the compression insert 414 into the receiver 410 through the U-shaped channel 464, with the arms 544 being located between the arms 462 during insertion of the insert 414 into the receiver 410, the insert 414 is lowered until the insert 414 is generally below the guide and advancement structures 472. The insert 414 is then rotated in a clock-wise direction into place about receiver 410 axis until the arms 544 are directly below the guide and advancement structures 472 and the protruding structures 484 abut against the rounded abutment walls 482 defining the receiver inner recesses 480. With particular reference to FIG. 44, after the insert 414 is rotated into such position, a tool (not shown) may be inserted into the receiver apertures 474 to press the thin receiver walls 478 into the insert grooves 556. The receiver 410 fully receives the compression insert 414 and blocks the structure 414 from spreading or splaying in any direction.

The assembled shank 404, retainer 412 and compression insert 414 are then implanted on a human spine in a manner identical or substantially similar to the manner previously described herein with respect to the assembly 1. Prior to insertion of the rod 421 into cooperating bone screw receivers 410, a pivot insert 416 is inserted into the U-shaped channel 464 of each of the receivers 410 and then into each compression insert 414 with the arms 584 of the pivot insert 416 aligned with the arms 544 of the pressure insert 414, as shown for example, in FIGS. 41 and 42, the arms 584 being received between the pair of saddle surfaces 546 until the body 582 bottom planar surface 583 of the pivot insert 416 seats on the planar surface 547 of the compression insert 414 and the cylindrical base 580 of the pivot insert 416 is received within the inner cylindrical surface 541 of the compression insert 414.

Figure 43:
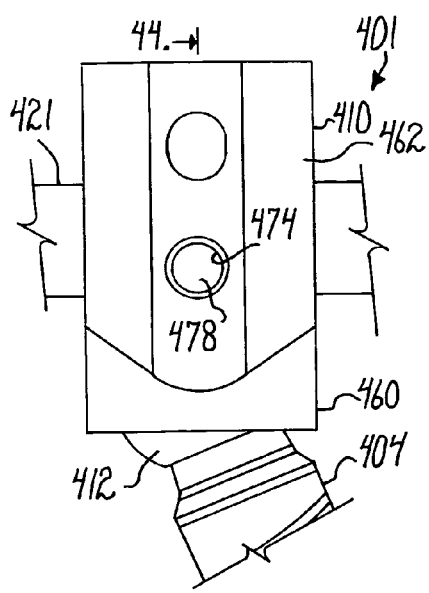
FIG. 43 is an enlarged and partial side elevational view of the assembly of FIG. 28 shown fully assembled with the rod.

With particular reference to FIGS. 43 and 47, the hard, inelastic, substantially non-deformable rod 421 is eventually positioned in an open or percutaneous manner in cooperation with at least two bone screw assemblies 401. Alignment of the rod surface 422 with the saddle surfaces 546 of the insert 414 is initially provided and then maintained by the frictionally mated surfaces 482 and 484 as well as by the crimped walls 478 of the receiver 410. The closure structure 418 is then inserted into and advanced between the arms 462 of each of the receivers 410. The closure structure 418 is rotated, using a tool engaged with the inner drive 566 until a selected pressure is reached at which point the rod 421 is captured between the saddle surfaces 546 of the compression insert 414 and frictionally engages both the curved elevated surface 590 of the pivot insert seating portion 589 and the convex surface 568 of the closure top 418. Also, as the closure structure 418 rotates and moves downwardly into the respective receiver 410, the rim 570 frictionally engages the top surfaces 545 of the arms of the compression insert 414. Thus, the closure top 418 presses against and biases the rod 421 into engagement with the pivot insert 416 that in turn presses against the compression insert 414 with the closure top 418 also pressing directly against the insert 414 to securely lock the polyaxial mechanism of the assembly 401 by fixing the shank 404 and the retainer 412 in a selected, rigid position relative to the receiver 410. At this time it is also possible for the retainer 412 to expand somewhat for an even tighter fit in the receiver cavity lower seat 494. With reference to FIGS. 45-47, it is also noted that in certain angular configurations of the shank 404 with respect to the receiver 410, the pivot insert spherical surface 579 also frictionally engages the shank upper spherical surface 440 when the rod 421 presses downwardly upon the pivot insert 416 due to downward force placed upon the rod 421 by the closure top 418.

Also with reference to FIGS. 45-47 various degrees of rod 421 angulation or toggle are shown. Specifically, FIGS. 45-47 illustrates various degrees of angulation in the sagittal plane of a 5.0 mm rod held between the pivot insert 416 curved surface 590 and the closure top 418 domed bottom surface 568. In particular, FIG. 45 illustrates no or zero degrees of angulation in the sagittal plane; FIG. 46 illustrates a rod angulation or toggle of three degrees and FIG. 47 illustrates a rod angulation or toggle of six degrees. Thus, the bone screw assembly 401 (as well as the bone screw assembly 201) advantageously provides for a semi-constrained, dynamic relationship between a non-deformable, hard rod and a polyaxial bone screw implanted in a human spine. Although the rod 421 is securely captured to the bone screw assembly 401 within the receiver 410, the rod 421 is free to move in the sagittal plane, being allowed an operative limited toggling or angulation in such plane. The rod can also be surrounded by a spacer which can abut up against the receivers and cooperate with the components to provide for dynamic spinal stabilization.

If removal of the rod 421 from any of the bone screw assemblies 401 is necessary, or if it is desired to release the rod 421 at a particular location, disassembly is accomplished by using the driving tool (not shown) that mates with the internal drive 566 on the closure structure 418 to rotate and remove such closure structure from the cooperating receiver 410. Disassembly is then accomplished in reverse order to the procedure described previously herein for assembly.

Bone screw assemblies according to the invention may also be used in a non-angulating, fully constrained or fixed manner with a hard, non-deformable rod, for example, when fusion is desired. With particular reference to FIGS. 48-50, a larger diameter rod, such as the illustrated rod 421' having an outer cylindrical surface 422' may be substituted for the rod 421 and used with the assembly 401 without the pivot insert 416 and with a different closure top 418'. Thus, in FIGS. 48-50, the resultant slightly different assembly is identified with the reference numeral 401'. The assembly 401' therefore includes the shank 404, the receiver 410, the two-piece retainer 412 and the compression insert 414 all previously described herein with respect to the assembly 401. The insert 414 is advantageously sized and shaped to closely receive the slightly larger diameter rod 421' as well as the rod 421 previously described herein. Specifically, the rod 421 illustrated with the assembly 401 has a diameter of 5 mm while the rod 421' illustrated with the assembly 401' has a diameter of 5.5 mm.

The closure top 418' is sized and shaped to mate with the receiver 410 at the guide and advancement structures 472, similar to the closure top 418 and only differs from the closure top 418 with respect to the size and surface features at a base thereof. Thus, the closure top 418' includes a guide and advancement structure 562', a top surface 564', an internal drive 566' and a bottom rim 570' that is the same or substantially similar to the respective guide and advancement structure 562, top surface 564, internal drive 566 and bottom rim 570 of the closure top 418. In lieu of the domed bottom surface 568 of the closure 418, the closure top 418' includes a planar bottom surface 567', downwardly extending rim 568' and downwardly extending point 569'. The rim 568' and point 569' are sized and shaped for engaging and penetrating the rod surface 422' as best illustrated in FIG. 50.

With reference to FIGS. 51-61, polyaxial bone screw assemblies according to the invention may also be used with softer, deformable and/or elastic longitudinal connecting members. The reference numeral 601 identifies such an assembly that includes the shank 404, the receiver 410, the two-piece retainer 412 and the compression or pressure insert 414 all previously described herein with respect to the assembly 401. The assembly 601 further includes a deformable and/or elastic pressure pad 616 and a closure structure or top 618 and is shown with a rod 621 made from a deformable material, for example, polyetheretherketone (PEEK). The pressure pad 616 may also be made from a non-metal material, such as PEEK. Both the pressure pad 616 and the rod 621 may be made from suitable plastic polymers, including, but not limited to ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. The pressure pad 616 fits within a portion of the compression insert 414 in a manner similar to the previously described pivot insert 416 of the assembly 401. However, the pressure pad 616 does not include an elevated seating portion or ridge. Rather, the illustrated pad 616 includes a substantially solid U-shaped seating surface that is preferably operationally located flush with or slightly above the U-shaped surfaces of the insert 414, the pad 616 functioning to cushion and closely and evenly hold the deformable rod 621 in position, the pad 616 also deforming, if needed, to provide such cushioning without causing undesirable deformation and stress on the rod 621 at the location where such rod is being held in place by the insert 414.

The closure top 618 is substantially similar in form and function to the top 418 previously described herein with respect to the assembly 401 with the exception that a bottom domed surface thereof includes a central projection and the domed surface and projection cooperate to firmly press against the deformable rod 621 and fix such rod in position without angular movement of the rod with respect to the closure top 618. Thus, the closure top 618 includes a guide and advancement structure 662, a top surface 664, an internal drive 666 a domed bottom surface 668 and a bottom rim 670 that are identical or substantially similar in form and function to the respective guide and advancement structure 562, top surface 564, internal drive 566, bottom domed surface 568 and bottom annular planar rim surface 570 of the closure top 418 previously described herein with respect to the assembly 401. The domed surface 668 further includes a centrally located downwardly directed projection in the form of a somewhat rounded point 671. As shown, for example, in FIGS. 60 and 61, the closure top 618 is sized and shaped so that the bottom rim 670 directly frictionally engages the top surface 545 of the compression insert 414, pushing the insert 414 in a direction toward the receiver base 460 so that the insert 414 directly frictionally engages the shank upper portion 408 at the spherical surface 440 pushing the shank 404 downwardly and thus pressing the retainer pieces 412 into frictional engagement with the receiver spherical seat 494. Therefore, locking of the polyaxial mechanism is not solely dependent upon the closure top 618 pressing on the deformable rod 621 that in turn presses the pressure pad 616 and the compression insert 414 into engagement with the shank 404.

With particular reference to FIGS. 54-58, the illustrated pressure pad 616 is sized and shaped to be received by and downloaded into the receiver 410 at the upper opening thereof, followed by insertion into the previously inserted compression insert 414. The pressure pad 616 has an operational central axis that is the same as the central axis of the receiver 410 and the compression insert 414. A concave, substantially spherical bottom surface 679 of the pressure pad 616 has a radius that is substantially the same or only slightly larger than the radius of the spherical body 438 of the upper portion 408 of the shank 404 and also substantially the same as the compression insert spherical surface 542, the surface 679 being sized and shaped to be slightly spaced from or slidingly receive the upper surface portion 440 of the spherical body 438 when the pressure pad 616 is seated within the compression insert 414 and before any downward pressure is placed on the pad 616 by the rod 621. The concave surface 679 partially defines an otherwise substantially cylindrical base 680 of the pressure pad 216, the base 680 including an annular bottom rim surface 681 disposed about the spherical surface 679. The base 680 is sized and shaped to be received within the inner cylindrical surface 541 of the compression insert 414. The base 680 is integral with an upper body portion 682 that has a planar somewhat rectangular-shaped bottom surface 683 that extends outwardly from either side of the base 680 and also forms a pair of upwardly extending arms 684. The upper body portion 682 further includes a U-shaped or saddle-like seating surface 685 spanning between the arms 684. Each of the arms 684 and the saddle seating surface 685 terminate at substantially planar, upper surfaces or strips 686. The arms 684 are sized and shaped to fit between the saddle surfaces 546 of the compression insert 414 with the bottom surface 683 being seated on the surface 547 of the compression insert 414. On either side of the saddle seating surface 685, the pressure pad upper body portion 682 is defined by opposed, slightly concave side surfaces 688, the surfaces 688 sloping slightly inwardly toward the cylindrical base 680 and then outwardly at the arms 684. A pair of opposed grooves 692 are formed in the saddle surface 685 and run through the arms 684 at a location centrally between and substantially parallel to the side surfaces 688. The illustrated grooves 692 have a dove-tail shape, allowing for ease of use by manipulation tools (not shown) for placement of the pressure pad 616 within the compression insert 414 (see FIGS. 52 and 53) and for disassembly therefrom, if needed.

In use, the shank 404, the retainer pieces 412 and the compression insert 414 of the assembly 601 are assembled in a manner identical or substantially similar to the manner of assembly previously described herein with respect to the shank 4, retainer pieces 12 and compression insert 14 of the assembly 1. The assembled shank 404, retainer 412 and compression insert 414 are then implanted on a human spine in a manner identical or substantially similar to the manner previously described herein with respect to the assembly 1. Prior to insertion of the rod 621 into cooperating bone screw receivers 410, a pressure pad 616 is inserted into the U-shaped channel 464 of each of the receivers 410 and then into each compression insert 414 with the arms 684 of the pressure pad 616 aligned with the arms 544 of the pressure insert 414, the arms 684 being received between the pair of saddle surfaces 546 until the planar surface 683 of the pressure pad 616 seats on the planar surface 547 of the compression insert 414 and the cylindrical base 680 of the pressure pad 616 is received within the inner cylindrical surface 541 of the compression insert 414.

Figure 59:
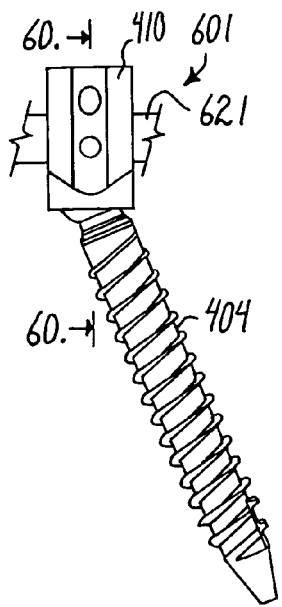
FIG. 59 is a reduced side elevational view of the assembly of FIG. 51.
Figure 60:
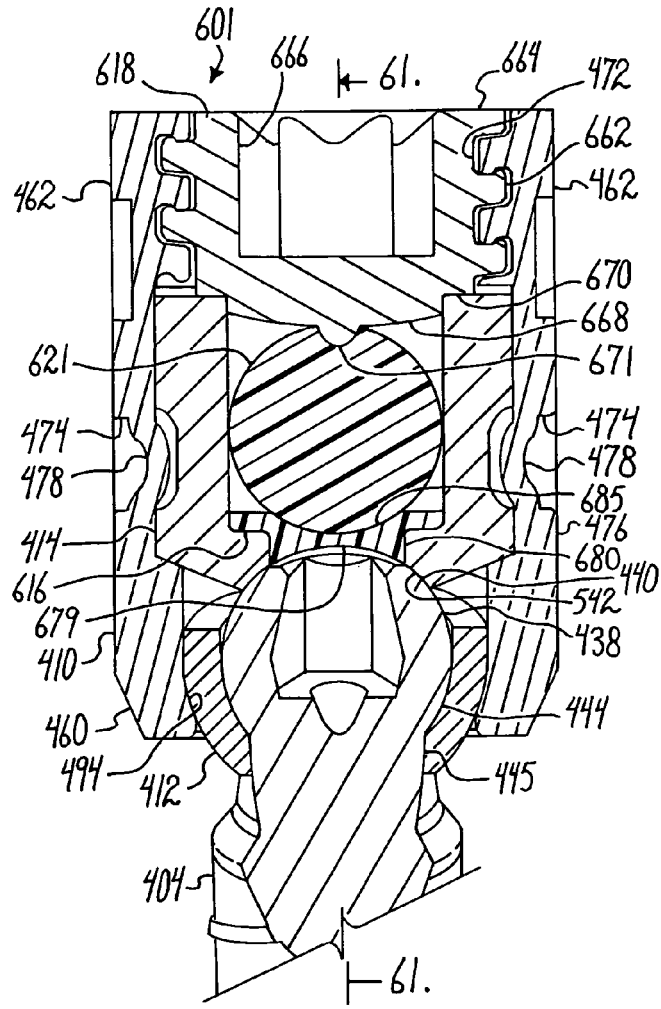
FIG. 60 is an enlarged and partial cross-sectional view taken along the line 60-60 of FIG. 59.
Figure 61:
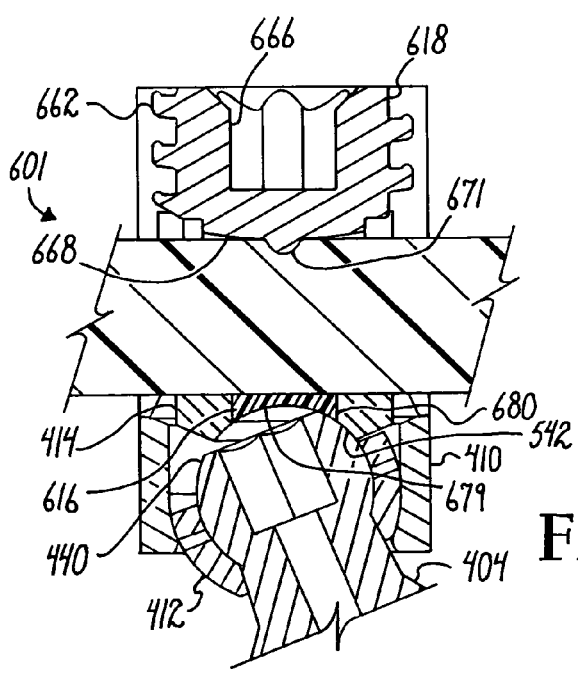
FIG. 61 is a reduced and partial cross-sectional view taken along the line 61-61 of FIG. 60.
Figure 62:
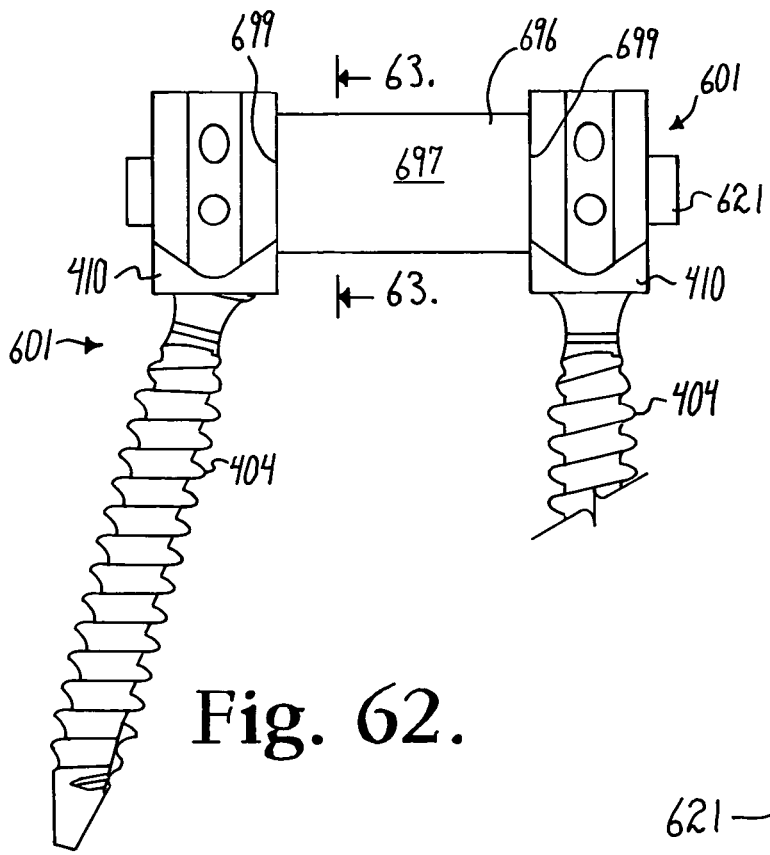
FIG. 62 is an enlarged and partial side elevational view of the bone screw assembly of FIG. 59 shown with a second bone screw of FIG. 59 attached to the rod and an elastic spacer located between the two bone screws.
Figure 63:
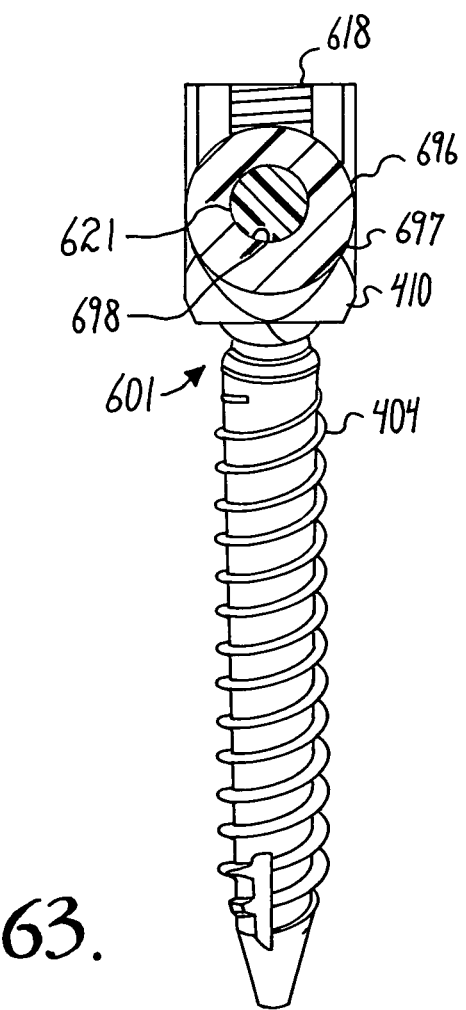
FIG. 63 is an enlarged cross-sectional view taken along the line 63-63 of FIG. 62.
Figure 64:
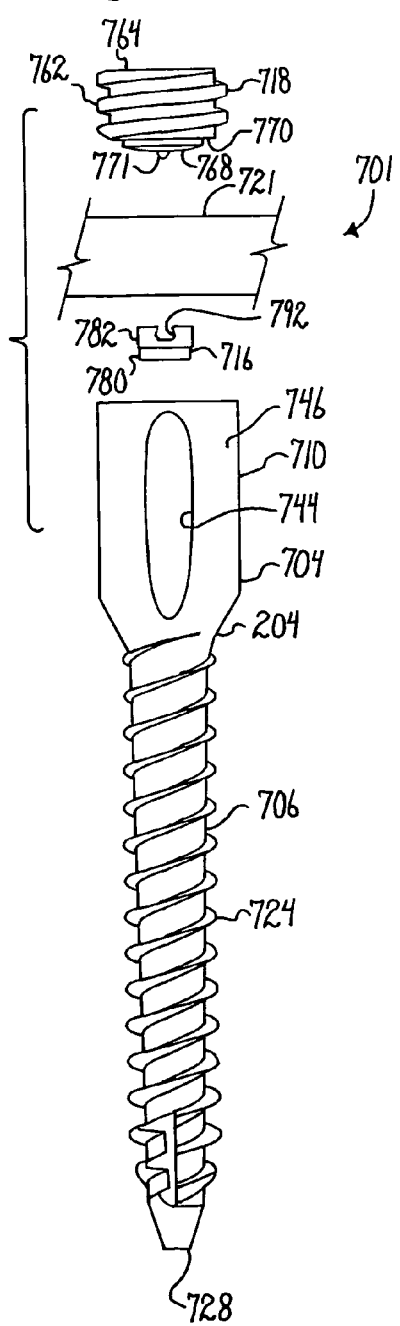
FIG. 64 is an enlarged exploded side elevational view of a fifth, alternative embodiment of a mono-axial bone screw assembly according to the present invention including a shank, a connecting member support insert, and a closure top, and further shown with a longitudinal connecting member in the form of a deformable rod.
Figure 65:
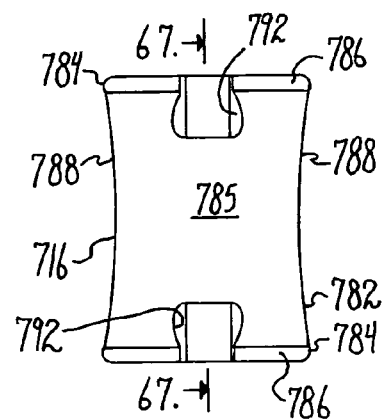
FIG. 65 is an enlarged top plan view of the support insert of FIG. 64.
Figure 66:
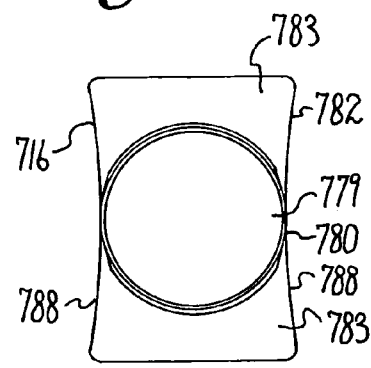
FIG. 66 is an enlarged bottom plan view of the support insert of FIG. 64.
Figure 67:
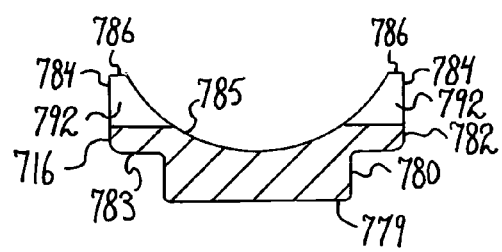
FIG. 67 is an enlarged cross-sectional view taken along the line 67-67 of FIG. 65.

With particular reference to FIGS. 59-61, and also with reference to FIGS. 62 and 63, the deformable rod 621, illustrated as a 5.5 mm diameter PEEK rod, is eventually positioned in an open or percutaneous manner in cooperation with the at least two bone screw assemblies 601. Alignment of the rod surface 622 with the saddle surfaces 546 of the insert 414 is provided by the frictional mating relationship between the receiver rounded wall 482 and the protruding wall 484 of the compression insert 414 and then further aided by the crimped walls 478 of the receiver 410. The closure structure 618 is then inserted into and advanced between the arms 462 of each of the receivers 410. The closure structure 618 is rotated, using a tool engaged with the inner drive 666 until a selected pressure is reached at which point the rod 621 is captured between the saddle surfaces 546 of the compression insert 414 and frictionally engages the saddle surface 685 of the pressure pad 616 with the closure top projection 671 and at least a portion of the domed surface 668 engaging the rod surface 622. The pressure pad 616 advantageously deforms and conforms to the rod surface 622, providing a secure, non-slip surface therebetween. The pad 616 cylindrical surface 680 that is received within the cylindrical surface 541 of the compression insert 414 also provides a secure non-slip engagement between the pad 616 and the insert 414. As the closure structure 418 continues to rotate and move downwardly into the respective receiver 410, the rim 670 frictionally engages the top surfaces 545 of the arms of the compression insert 414, the insert 414 pressing against the shank upper domed surface 440, the shank pressing against the retainer pieces 412 and the retainer pieces frictionally engaging the receiver at the seating surface 494 to securely lock the polyaxial mechanism of the assembly 601 by fixing the shank 404 and the retainer 412 in a selected, rigid position relative to the receiver 410. The torque required to secure the polyaxial mechanism does not cause undue deformation to the rod 621 due to the advantageous cushioning provided by the deformable pressure pad 616. Furthermore, the compression insert 414 is not twisted out of alignment due to the secure, close engagement between the compression insert protruding surfaces 484 and the retaining walls 482 of the recesses in the receiver 410. At this time it is also possible for the retainer 412 to expand somewhat for an even tighter fit in the receiver cavity lower seat 494.

If removal of the rod 621 from any of the bone screw assemblies 601 is necessary, or if it is desired to release the rod 621 at a particular location, disassembly is accomplished by using the driving tool (not shown) that mates with the internal drive 666 on the closure structure 618 to rotate and remove such closure structure from the cooperating receiver 410. Disassembly is then accomplished in reverse order to the procedure described previously herein for assembly.

With particular reference to FIGS. 62 and 63, it is noted that a deformable or elastic rod 621 according to the invention may advantageously cooperate with an elastic or inelastic spacer 696 slidingly received about the rod 621 and located between a pair of bone screws 601, the illustrated spacer 696 being in contact with side surfaces of each of the illustrated bone screws 601. The illustrated spacer 696 is tubular having an outer cylindrical surface 697 and an inner cylindrical surface 698 forming a through bore sized and shaped to slidingly receive the rod 621 therethrough. The illustrated spacer includes opposed side surfaces 699, one or both of which may be cut-to-length by the surgeon for a desired close fit between the bone screws 601. The spacer 696 may be compressed between the bone screws 601, followed by tightening of the closure tops 618 onto the deformable rod 621. Spacers of the invention may take other shapes, including, but not limited to other curved and polygonal shapes having substantially central or off-set through bores for receiving the rod 621 therethrough.

With reference to FIGS. 64-70 an alternative mono-axial bone screw assembly according to the invention, generally 701 is illustrated. The assembly includes a bone screw body 704 having a threaded shank 706 integral or fixed to a head or receiver 710; a deformable pressure pad 716; and a closure top 718, and further shown with a longitudinal connecting member in the form of a deformable rod 721 having an outer cylindrical surface 722. The illustrated deformable rod 721 for use with the assembly 701 is similar in form, function and material as the rod 621 previously described herein with respect to the assembly 601, being preferably cylindrical in shape and made from PEEK. It is noted however, that longitudinal connecting members made from other materials and geometries and used with or without cooperating outer spacers may be used with assemblies 701 of the invention, the receiver 710 and pressure pad 716 having alternative inner geometries sized and shaped for closely receiving such longitudinal connecting members.

The shank body 724 is elongate, having a helically wound bone implantable thread 724 extending from near a neck 726 located near the receiver 710 to a tip 728 of the body 706 and extending radially outwardly therefrom. During use, the body 706 utilizing the thread 724 for gripping and advancement is implanted into a vertebra leading with the tip 728 and driven down into the vertebra with an installation or driving tool (not shown), so as to be implanted in the vertebra to near the neck 726.

The neck 726 extends axially upward from the shank body 706 to the integral receiver 710. The shank body 706 shown in the drawings is cannulated, having a small central through bore 729 extending an entire length of the shank body 706 along a central axis thereof from the receiver 710 to the tip 728. The bore 729 provides a passage through the shank 704 interior for a length of wire (not shown) inserted into a vertebra prior to the insertion of the shank body 706, the wire providing a guide for insertion of the shank body 706 into a vertebra (not shown).

To provide a biologically active interface with the bone, the threaded shank body 706 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or on-growth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figure 70:
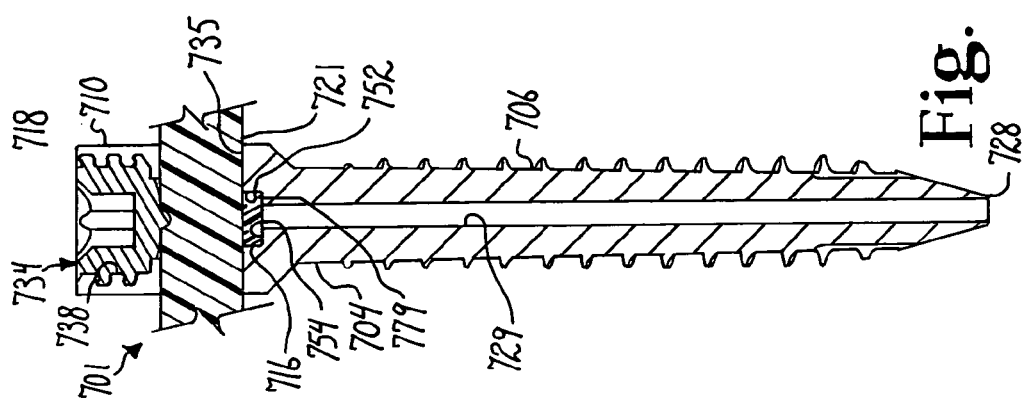
FIG. 70 is an enlarged cross-sectional view taken along the line 70-70 of FIG. 69.
Figure 69:
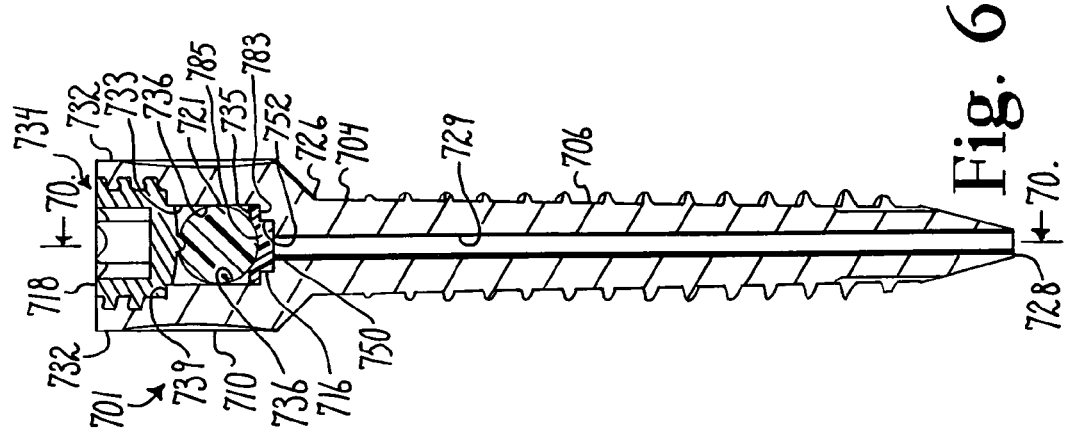
FIG. 69 is an enlarged cross-sectional view taken along the line 69-69 of FIG. 68.
Figure 68:
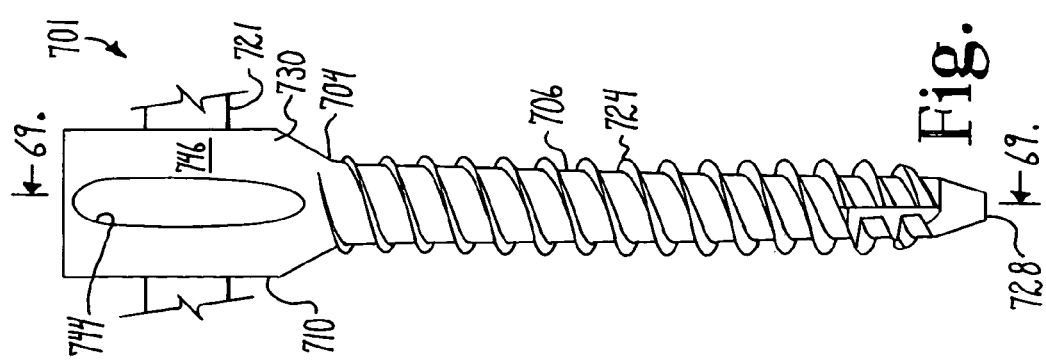
FIG. 68 is an enlarged side elevational view, similar to FIG. 64, showing the bone screw assembly of FIG. 64 assembled.

With particular reference to FIGS. 68-70, the receiver 710 includes a base 730 integral with a pair of opposed upstanding arms 732 defining a squared-off channel 733 between the arms 732 with an upper opening, generally 734, and a lower planar seat 735, the channel 733 having a width for operably snugly receiving the rod 721 between the arms 732 at lower opposed substantially planar side surfaces 736. Each of the arms 732 also has an interior surface that defines an inner cylindrical profile that includes a partial helically wound guide and advancement structure 738. In the illustrated embodiment, the guide and advancement structure 738 is a partial helically wound interlocking flange form configured to mate under rotation with a similar structure on the closure structure 718, as described more fully below. However, it is foreseen that the guide and advancement structure 738 could alternatively be a square-shaped thread, a buttress thread, a reverse angle thread or other thread-like or non-thread-like helically wound discontinuous advancement structure for operably guiding under rotation and advancing the closure structure 718 downward between the arms 732. Run-out top surfaces 739 partially defined by the planar arm surfaces 736 form a stop for the closure structure 718, providing a secure mechanism for locking such closure 718 when used with deformable longitudinal connecting members such as the rod 721.

An opposed pair of tool receiving and engaging apertures 744 are formed on outer surfaces 746 of the arms 732. The apertures 744 are used, for example, with a driving tool (not shown) for rotating the bone screw body 704 into a vertebra (not shown).

Communicating with the channel 733 of the receiver 710 is a chamber or cavity 750 defined by a substantially cylindrical inner surface 752 and an annular base 754 disposed substantially perpendicular to the inner cylindrical surface 752. The cavity 750 also communicates with the cannulation bore 729.

The closure top 718 is substantially similar in form and function to the top 618 previously described herein with respect to the assembly 601. Thus, the closure top 718 includes a guide and advancement structure 762, a top surface 764, an internal drive 766 a domed bottom surface 768 a bottom rim 770 and a bottom projection 771 that are identical or substantially similar in form and function to the respective guide and advancement structure 662, top surface 664, internal drive 666, bottom domed surface 668, bottom annular planar rim surface 670 and bottom projection 671 of the closure top 618 previously described herein with respect to the assembly 601. As shown, for example, in FIGS. 69 and 70, the closure top 718 is sized and shaped so that after the domed surface 768 and projection 771 fully engage the deformable rod 721, the bottom rim 770 directly frictionally engages the surface 739 of the bone screw receiver 710, locking the closure top 718 in place independently of the rod 721. Therefore, locking of the closure top 718 is not solely dependent upon the closure top 718 pressing on the deformable rod 721.

With particular reference to FIGS. 64-68, the illustrated pressure pad 716 is sized and shaped to be received by and downloaded into the receiver 710 at the upper opening 734 thereof, followed by partial insertion into the cavity 750. The pressure pad 716 is substantially similar in form and function and made from materials similar to the pad 616 previously described herein with respect to the assembly 601 with the exception that the pad 716 has a planar bottom surface 779 in lieu of the spherical surface 679 of the pad 616. Thus, the pad 716 includes a cylindrical base 780, an upper body 782 with a substantially planar rectangular bottom surface 783, a pair of opposed arms 784, a saddle seating surface 785, planar arm top surfaces 786, opposed side surfaces 788 and through grooves 792 that are the same or substantially similar in form and function to the cylindrical base 680, upper body 682 with substantially planar rectangular bottom surface 683, pair of opposed arms 684, saddle seating surface 685, planar arm top surfaces 686, opposed side surfaces 688 and through grooves 792 of the pressure pad 616 of the assembly 601 previously described herein.

In use, the pressure pad 716 is assembled with the bone screw 704 by inserting the pad into the channel 733 of each of the receivers 710 and then into each cavity 750 with the arms 774 of the pressure pad 716 aligned with the arms 732 of the receiver 710 and the pad 716 moved downwardly until the planar surface 783 of the pressure pad 616 seats on the planar surface 735 of the receiver 710 and the cylindrical base 780 of the pressure pad 716 is received within the inner cylindrical surface 752 defining the receiver cavity 750 and the base 779 of the pad 716 also seats upon or is disposed near the annular surface 754 of the receiver 710. The assembled shank bone screw body 704 and pressure pad 716 are then implanted on a human spine by rotation of the shank body 706 into bone, preferably utilizing a guide wire (not shown) extending through the cannulation bore 729, a driving tool (not shown) being engaged with the apertures 744.

With particular reference to FIGS. 69 and 70, the deformable rod 721, is eventually positioned in an open or percutaneous manner in cooperation with the at least two bone screw assemblies 701. The closure structure 718 is then inserted into and advanced between the arms 732 of each of the receivers 710. The closure structure 718 is rotated, using a tool engaged with the inner drive 766 until a selected pressure is reached at which point the rod 721 engages the saddle surface 785 of the pressure pad 716 with the closure top projection 771 and at least a portion of the domed surface 768 engaging the rod surface 722. The pressure pad 716 advantageously deforms and conforms to the rod surface 722, providing a secure, non-slip surface therebetween. As the closure structure 718 continues to rotate and move downwardly into the respective receiver 710, the rim 770 frictionally engages the stop top surfaces 739 located directly below the guide and advancement structures 738, locking the closure top 718 to the bone screw receiver 710 without causing undue deformation to the rod 721 due to the advantageous cushioning provided by the deformable pressure pad 716.

If removal of the rod 721 from any of the bone screw assemblies 701 is necessary, or if it is desired to release the rod 721 at a particular location, disassembly is accomplished by using the driving tool (not shown) that mates with the internal drive 766 on the closure structure 718 to rotate and remove such closure structure from the cooperating receiver 710. Disassembly is then accomplished in reverse order to the procedure described previously herein for assembly.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly comprising:
a) a shank having an elongate body and an upper portion, the body being configured for fixation to a bone, the shank supper portion having a lower neck and an upper region that extends radially outward from the neck and has a lower semispherical surface;
b) a receiver having a top portion and a base, the receiver top portion having an upper channel adapted to receive a longitudinal connecting member, the base having an internal seating surface partially defining a cavity, the channel communicating with the cavity, the cavity communicating with an exterior of the base through an opening; the shank upper portion being received through the opening and positioned within the cavity;
c) a retainer having an inner surface and an outer surface, the retainer inner surface configured to be in pivotal engagement with the shank upper portion semispherical surface and the retainer outer surface configured to be in engagement with the receiver seating surface when the retainer is captured between the shank upper portion and the seating surface, the retainer preventing the shank upper portion from passing through the receiver opening allowing the shank to move polyaxially relative to the receiver during positioning, the retainer includes two discrete portions that are not joined together.

2. The assembly according to claim 1 including:
a) a compression insert disposed within the receiver, the insert being sized and shaped to frictionally engage the shank upper portion.

3. The assembly according to claim 2 including:
a) at least one of a pivot insert and a compression pad located in a recess of the compression insert and having a surface adapted to engage a longitudinal connecting member received in the channel.

4. A polyaxial bone screw assembly comprising:
a) a shank having an elongate body and an upper portion, the body being configured for fixation to a bone;

b) a receiver having a top portion and a base, the receiver top portion having a channel adapted to receive a longitudinal connecting member, the base having an internal seating surface partially defining a cavity, the channel communicating with the cavity, the cavity communicating with an exterior of the base through an opening;

c) a retainer having an inner surface and an outer surface, the inner surface configured to be engagement with the shank upper portion and the outer surface configured to be in engagement with the receiver seating surface when the retainer is captured between the shank upper portion and the seating surface, cooperating to prevent the shank upper portion from passing through the receiver opening; the retainer having two separate portions that are not physically joined together but abut against each other and the shank;

d) a compression insert disposed within the receiver and configured to frictionally engage the shank upper portion and adapted to engage the connecting member.

5. A polyaxial bone screw assembly comprising:

a) a shank having an elongate body and an upper portion, the body being configured for fixation to a bone;

b) a receiver having a top portion and a base, the receiver top portion defining a channel to receive a longitudinal connecting member, the base having an internal seating surface partially defining a cavity, the channel communicating with the cavity, the cavity communicating with an exterior of the base through an opening sized and shaped to upwardly load the shank upper portion through the opening;

c) a retainer having an inner surface and an outer surface, the inner surface configured to be in engagement with the shank upper portion and the outer surface configured to be in engagement with the receiver seating surface when the retainer is captured between the shank upper portion and the seating surface, the retainer preventing the shank upper portion from passing down through the receiver opening and the retainer moving with the shank in polyaxial rotation with respect to the receiver;

d) a compression insert disposed within the receiver the insert sized and shaped to frictionally engage the shank upper portion at a location spaced from the retainer;

e) a discrete compression pad located in a recess of the compression insert and having a first surface engaging a longitudinal connecting member and an opposed second surface engaging the shank upper portion.

6. A polyaxial bone screw assembly comprising:

a) a shank having an elongate body and an upper portion, the body being configured for fixation to a bone;

b) a receiver having a top portion and a base, the receiver top portion defining a channel to receive a longitudinal connecting member, the base having an internal seating surface partially defining a cavity, the channel communicating with the cavity, the cavity communicating with an exterior of the base through an opening;

c) a retainer having an inner surface and an outer surface, the inner surface configured to be in engagement with the shank upper portion and the outer surface configured to be in engagement with the receiver seating surface when the retainer is captured between the shank upper portion and the seating surface, the retainer preventing the shank upper portion from passing down through the receiver opening and the retainer moving with the shank in polyaxial rotation with respect to the receiver;

d) a compression insert disposed within the receiver, the insert being sized and shaped to frictionally engage the shank upper portion; and e) a discrete compression pad located in a recess of the compression insert and having a surface engaging a longitudinal connecting member.

* * * * *